United States Patent [19]

Sakai et al.

[11] Patent Number: 5,203,984

[45] Date of Patent: Apr. 20, 1993

[54] MONITORING SYSTEM FOR PLANT OPERATION CONDITION AND ITS IN-SITU ELECTROCHEMICAL ELECTRODE

[75] Inventors: Masanori Sakai; Katsumi Mabuchi, both of Hitachi; Toshiaki Arato, Katsuta; Takuya Takahashi, Hitachi; Masakiyo Izumiya, Mito; Isao Masaoka, Hitachi; Yoshitaka Kojima, Hitachi; Masahisa Inagaki, Hitachi; Katsumi Ohsumi, Hitachi; Makoto Hayashi, Hitachi; Fumio Sato, Hitachi; Masateru Suwa, Tohkai; Kimihiko Akahori, Katsuta, all of Japan

[73] Assignee: Hitachi, Ltd., Tokyo, Japan

[21] Appl. No.: 573,780

[22] Filed: Aug. 28, 1990

[30] Foreign Application Priority Data

Sep. 11, 1989 [JP] Japan ................... 1-232824

[51] Int. Cl.$^5$ ............................... G01N 27/26
[52] U.S. Cl. ........................ 204/435; 204/433
[58] Field of Search ............ 204/153.1, 400, 433, 204/435

[56] References Cited

U.S. PATENT DOCUMENTS

| | | | |
|---|---|---|---|
| 4,338,175 | 7/1982 | Binder et al. | 204/433 |
| 4,575,410 | 3/1986 | Neti | 204/433 |
| 4,636,292 | 1/1987 | Fejes et al. | 204/435 |
| 4,857,158 | 8/1989 | Cawlfield | 204/433 |
| 4,937,038 | 6/1990 | Sakai et al. | 204/153.1 |

Primary Examiner—John Niebling
Assistant Examiner—Bruce F. Bell
Attorney, Agent, or Firm—Antonelli, Terry, Stout & Kraus

[57] ABSTRACT

A plant operational status monitoring supervisory system comprising; means for extracting information directly relating to water quality of an objective portion consecutively for a period of time by means of an electrochemical water quality sensor installed in an objective portion to monitor in-situ in a plant; means for evaluating water quality based on thus extracted information; means for comparing an obtained water quality evaluation result with a reference value for a predetermined plant operation procedure; and means for displaying or storing necessary portion out of said comparison results; is disclosed.

An electrochemical reference electrode used in this system being provided with an electrolyte layer containing ion of the electrode member; a porous ceramic layer surrounding the same without permeating liquid; and electrode member electrochemically contacting with said elec-trolyte layer; and a terminal electrically contacting with said electrode member; and further having a long life in high temperature water, various status of high temperature water in objective portions and that of nearby constituent members in a plant are possible to be monitored online by means of this reference electrode.

Further, because monitored data are processed by means of a neural network, the higher precision level of monitoring has been achieved.

16 Claims, 14 Drawing Sheets

MONITORING SYSTEM FOR PLANT OPERATION CONDITION AND ITS IN-SITU ELECTROCHEMICAL ELECTRODE

BACKGROUND OF THE INVENTION

1. Field of the invention

The present invention relates to a monitoring system for plant operating conditions in which water quality data of such as nuclear power and thermal power plants are sampled in-situ and thereby diagnosis of high reliability is effected.

2. Prior Art

Japanese Patent Application Laid Open No. 58-51312 (1983) and U.S. Pat. No. 4,552,718 disclose monitoring devices for plant operation.

However, in the above Japanese Patent Application Laid-Open No. 58-51312 (1983) no method of obtaining information relating to water quality, no method of water quality evaluation information and no monitoring and controlling system of the plant in which the information from the respective water quality sensors is evaluated totally and water quality is monitored and controlled are disclosed. Further, U.S. Pat. No. 4,552,718 discloses in detail a method and system for plant operation control with regard to the status amount (output amount, cooling water level, temperature in reactor, etc.,) of a nuclear power plant operation. However, it does not disclose a water quality diagnosis and control system and technology which evaluate totally such as a sensing method of water quality itself, an evaluation method and a display system.

Japanese Patent Application Laid-Open No. 60-183595 (1985) discloses a plant operating method wherein observing pH (hydrogen ion concentration) of a nuclear reactor cooling water, pH of the cooling water is adjusted within a range between 7.0 and 8.5, but neither specify technology with regard to a pH sensor, nor clarify the relationship between the pH and other water quality information and further does not specify a display method during control.

ECP sensors (reference electrodes or corrosion potential sensor) in a high temperature and high pressure water is discussed in "Reference Electrode for PWR, Copyright 1987 Electric Power Research Institute, Inc." which is a comprehensive paper in recent years dealing the reference electrodes in a high temperature and high pressure water. The ECP sensor of Ag/AgCl (silver/silver chloride) which is employed for use in this paper has a structure wherein the silver/silver chloride regardless to an inner reference electrode or an outer reference electrode is immersed in a solution including $Cl^-$ (chlorine ion).

The Ag/AgCl electrodes are fundamental and representative reference electrodes for electrochemical measurement and these electrodes have a small temperature coefficient and have been used for the high temperature and high pressure water until now. However, under the severe environment such as the high temperature and high pressure water it was a problem that the sensor itself is deteriorated by potential variation due to the leakage of the $Cl^-$ ion accompanied with the deterioration of water seal in particular, there were no ECP sensors which were disposed in a nuclear reactor and had a life time level enduring the use in a periodic inspection interval.

The hydrogen ion concentration sensor in the high temperature and high pressure water is discussed in "Journal of Electrochemical Society, 132, 1866 (1985)" the problem is how to seal it or how to improve the durability of sensor itself which problem arises during disposing thereof in the reactor, wherein since the pH is measured by use of no liquid junction, isolating from the high temperature environment in a ceramic (of which porous ratio is near zero) cylinder and making use of the semiconductor property of the ceramic, its impedance becomes extremely high and there remain problems such as a counter measure to noise and an isolation method between the cylinder interior and the high temperature water environment.

With regard to an evaluation method of measured results and a display method, the above Japanese Patent Application Laid-Open No. 58-51312 (1983) also discloses a measure for displaying plant status amount during plant operation such as nuclear reactor pressure and cooling water level on the CRT of a computer as a specific screen image, however in this case again no technology with regard to sensing of the respective states and to monitoring of the water quality information is referred to, and further no indication is made on the measure which water quality information to be combined and how these to be evaluated.

Further no consideration on the sensor technology was made when controlling the water quality by monitoring the water quality and feeding back the water quality data to the control system, so that there was an actual problem that the water quality monitoring system and control system itself was impracticable due to the incredibility of the obtained data and the durability of the sensors. Therefore because of no credible sensors the system was limited to a plant operation and control based on the mechanical sides and status amount of the plant, no consideration from total point of view was made based upon an evaluation and plant method based on a technology which measures and controls the very water quality factors, an evaluation method based on a monitoring data display system and a displayed screen image, and other status amounts such as an abnormal sound of a pump and water quality status amount near the pump such as temperature and the results of water quality monitoring data, accordingly there was a technical problem that the plant control method could not operate the plant with necessary and sufficient information.

In Japanese Patent Laid-Open No. 58-215549 (1984), there is disclosed an electrochemical partitioned by a diaphragm and filled with electrolyte therein. However, for use in such environments as in a nuclear power plant or thermal power plant where stringent quality control of high temperature water is necessary, heat resistance and durability of the same are not satisfactory, confronting practical applications.

As disclosed in Japanese Patent Laid-Open No. 58-215549 (1983), means for separation and determination of dissolved hydrogen may be effective. In this case, however, because a selective hydrogen permeating membrane is required, there will still arise the like problem.

In the Electrochemical Method, John Willy & Sons, Inc. (1980) pp. 553-573, an electrochemical measurement apparatus for use in a nuclear power plant is described. However, there is no description on an electrochemical cell capable of being installed incore of a nuclear plant or in a piping system of a plant, and further having a low impedance reference electrode characteristic.

SUMMARY OF THE INVENTION

The first object of this invention is to provide means for extracting information with high precision on high temperature water quality essential for monitoring operational conditions in a nuclear power plant or thermal power plant where high temperature water is used.

The second object of this invention is to provide means for obtaining precise and adequate information directly relating to water quality from a plant in operation.

The third object of this invention is to provide a system capable of controlling water quality specifically by means of predicting status changes in a plant from a comparison between existing water information and accumulated monitoring data.

BRIEF DESCRIPTION OF THE DRAWINGS

FIG. 18($b$) is a graph illustrating random pulse signals to apply to a work electrode in an electrochemical sensor.

DETAILED DESCRIPTION OF THE INVENTION

Figure 1:
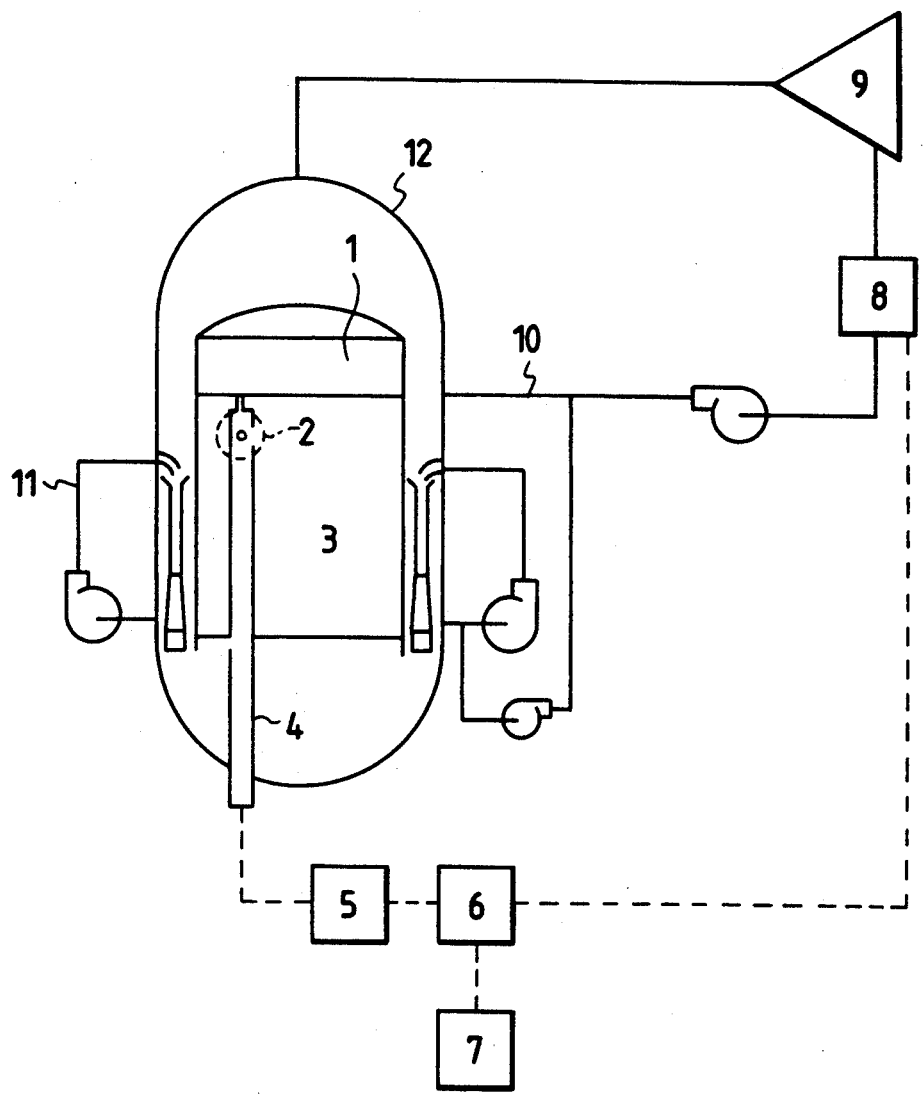
FIG. 1 is a schematic diagram illustrating a plant operating condition monitoring system in which the present invention is employed in a nuclear power plant.

For achieving the above objects, the present invention proposes a monitoring system for plant operating conditions, which comprises means for sampling consecutively information directly relating to water quality of an objective section of the monitoring plant in a predetermined period through an electrochemical water quality sensor disposed in said objective monitoring section of the plant; means for evaluating the water quality based on the sampled information; means for comparing the obtained water quality evaluation result with a predetermined reference value for the plant operation and manipulation; and means for displaying or recording necessary portions of said comparison result.

The above water quality sensor is disposed in the objective monitoring section of the plant through a porous material which permits electrochemical contact between the high temperature water in the objective monitoring section and an electrolyte of the sensor but suppresses excessive dissolution of the electrolyte into the high temperature water. The porous ceramic or resin covering material is non-liquid-permeable but ion-permeable. That is, the covering material prevents liquid from going through the material into the electrolyte, but allows liquid to be in electrochemical contact with the electrolyte. Only ions of the electrolyte can come out through the covering material.

Through the disposition of the electrochemical water quality sensor in an objective monitoring section of the plant, developing a reference electrode (ECP sensor) and pH sensor (hydrogen ion concentration meter) with high durability, high reliability and actual attaching facility, and by developing an electrochemical cell or sensor capable of determining dissolved oxygen, hydrogen peroxide and the like by using the reference electrode thereof, and using in combination with various water quality data (pH, corrosion potential, dissolved oxygen, dissolved hydrogen, dissolved hydrogen peroxide, electrical conductivity of solution, etc.) based on the electrochemical measurement, and the other crack sensor, a measure as a sensor system is established.

A structure of an electrochemical reference electrode for use in the present invention is characterized by comprising an electrolyte layer containing ion of the electrode, a porous ceramic layer surrounding the electrolyte layer preventing liquid permeance, an electrode member electrochemically contacting with said electrolyte, and a terminal electrically contacting with said electrode member. By this structure, impedance of the reference electrode has been successfully decreased low enough as an electrochemical cell, providing an electrochemical sensor comprising a three electrode system of a work electrode, a counter electrode and a reference electrode, or a two electrode system thereof.

Further, a heat resistant porous jacket layer surrounding the ceramic layer and preventing liquid permeance may also be provided. Still further, there may be used an electrochemical reference electrode comprising an electrolyte layer composed of halogenated substance of the electrode, a porous ceramic layer preventing liquid permeance and surrounding the same, an electrode member electrochemically contacting with the electrolyte layer, a sheath protecting the ceramic layer and having part of the same exposed therethrough allowing part of the ceramic layer to contact with water to measure, and a terminal electrically contacting with the electrode member.

As an exemplary embodiment of the structure of an electrochemical reference electrode, there is one comprising a solid electrolyte layer containing positive ion and negative ion of an electrode member, a porous ceramic layer surrounding the same, a porous insulation layer preventing liquid permeance but allowing ion permeance and surrounding said porous ceramic layer, a metal electrode member electrochemically contacting with the electrolyte layer, a sheath jacket protecting the ceramic layer and having part thereof exposed open for allowing part of the ceramic layer to communicate with water to measure, and a terminal electrically contacting with said electrode member. As a solid electrolyte layer, a combination of an oxide of the electrode metal member/metal as well as halogenated metal/metal may be used.

The inventors enabled the water quality diagnosis and the water quality control through development of a compact ceramic coated type sensor of adjustable porous ratio with sufficient accuracy and durability, and an electrochemical sensor having a reference electrode of the present invention as its sensor, through mutual study of data in-situ obtained from possible series of system constitution using the developed sensor and through improvement of the evaluation method into more specific and systematic manners.

The water quality diagnosis data which are monitored by an arithmetic processing unit and displayed on a CRT display adequately indicates water quality information with the ceramic coated or resin coated type sensor system and does not provide erroneous information, thereby, operators enable proper operation and administration of the water quality and the plant by immediately feeding back the results obtained from the water quality display system to the plant water quality operation control.

Through establishment of the water quality information acquiring technology with adequate and high accuracy from the sensor system, mutual relationship of data, display system and evaluation standard are possibly determined and an operation and administration of water quality and plant with a higher standard are enabled.

The single or plural sensors have a structure in which electrodes of silver/halogenated silver, silver sulfate or single silver electrodes are overcoated tightly with press-formed ceramics or resin microscopic powders, or are directly coated at their surface with a ceramic material having a solution impregnatable aperture ratio through measures such as a direct plasma spray, electrophoresis method, combination of the both and etc., so that through a measure not immersing in a solution of halogenated ions the present sensor is used as a sensor indicting a potential of the standard electrode (reference electrode or ECP sensor).

Further as the pH sensor such sensor is used in which silver/silver oxide, platinum/thallic oxides ($Tl_2O_3$), mercury/mercury oxide, copper/copper oxide, indium-/$Ir_2O_3$, and is directly coated by ceramics or by press-formed ceramics or resin microscopic powders and is constituted so as to respond by potential corresponding to pH (hydrogen ion concentration in solution). In principle, the pH sensor suffices the function of the ECP sensor when a pH condition is constant or variation of pH is negligible. Disposition of both the above ECP sensor and the pH sensor, is practical.

It is preferable to dispose either the ECP sensor of pH sensor, both thereof or pural thereof at the vicinity of a nuclear reactor core and instrumentation piping, a separator or its vicinity, a mixing plenum or its vicinity, a down comer or its vicinity, a jet pump or its vicinity, a downstream plenum or its vicinity or a cooling water piping line.

In the plant piping line of the reactor is disposed a measure for controlling water quality by injecting a gas such as oxygen and hydrogen or chemicals.

A measure for electrochemically analyzing dissolved chemical species existing in a solution may be provided which respectively uses at least one of a three electrode system composed of one working electrode, a reference electrode (ECP sensor) and a counter electrode and a two electrode system employing two electrodes of the three.

All of the water quality analysis, the data reading of the analyzed results and the display are carried out by using an arithmetic processing unit, a printer, a plotter, and a cathode ray tube display system (CRT). The water quality sensors totaling to seven kinds which includes the crack sensor, in that, sensors of dissolved hydrogen (DH), dissolved oxygen (DO), (pH), (ECP), solution electric conductivity (S) and dissolved hydrogen peroxide $DH_2O_2$ are disposed while combining thereof properly (herein below abbreviated the crack sensor as (M), the dissolved hydrogen as (DH), the dissolved oxygen as (DO), the solution electric conductivity as (S) and the dissolved hydrogen peroxide as ($DH_2O_2$)). The water quality diagnosis control is carried out by selecting water quality diagnosis data from two kinds of sensors among the seven sensors and comparing and examining with a standard value inputted before hand based on the display of the cathode ray tube display system, the printer, the plotter and the recorder.

The water quality diagnosis control can be carried out based on the display of the CRT, the printer, the plotter and the recorder on (DO) and (ECP). All the water quality analysis, the data reading of the analyzed results and the display are carried out by using an arithmetic processing unit, a printer, a plotter, and a cathode ray tube display system (CRT).

A plurality of sensors such as the crack sensor measuring crack development amount, the dissolved hydrogen sensor, the dissolved oxygen sensor, the corrosion potentiometer or the reference electrode (ECP sensor), the solution electric conductivity meter and the dissolved hydrogen peroxide are used in combination under a water quality environment.

Several examples of sensor combination and their combination with the display measures are explained below;

(1) A water quality diagnosis control is carried out based on the display of the CRT, the printer, the plotter and the recorder on (DH) and (DO).

(2) A water quality diagnosis control is carried out based on the display of the CRT, the printer, the plotter and the recorder on (DH) and (pH).

(3) A water quality diagnosis control is carried out based on the display of the CRT, the printer, the plotter and the recorder on (DH) and the solution electric conductivity (S).

(4) A water quality diagnosis control is carried out based on the display of the CRT, the printer, the plotter and the recorder on (DH) and the crack development amount (M) of the crack sensor.

(5) A water quality diagnosis control is carried out based on the display of the CRT, the printer, the plotter and the recorder on (DH) and ($DH_2O_2$).

(6) A water quality diagnosis control is carried out based on the display of the CRT, the printer, the plotter and the recorder on (DH) and (pH).

(7) A water quality diagnosis control is carried out based on the display of the CRT, the printer, the plotter and the recorder on (DO) and (S).

(8) A water quality diagnosis control is carried out based on the display of the CRT, the printer, the plotter and the recorder on (DO) and (M).

(9) A water quality diagnosis control is carried out based on the the display of the CRT, the printer, the plotter and the recorder on (DO) and ($DH_2O_2$).

(10) A water quality diagnosis control is carried out based on the display of the CRT, the printer, the plotter and the recorder on (DO) and (ECP).

(11) A water quality diagnosis control is carried out based on the display of the CRT, the printer, the plotter and the recorder on (pH) and (ECP).

(12) A water quality diagnosis control is carried out based on the display of the CRT, the printer, the plotter and the recorder on (pH) and (S).

(13) A water quality diagnosis control is carried out based on the display of the CRT, the printer, the plotter and the recorder on (pH) and (M).

(14) A water quality diagnosis control is carried out based on the display of the CRT, the printer, the plotter and the recorder on (pH) and ($DH_2O_2$).

(15) A water quality diagnosis control is carried out based on the display of the CRT, the printer, the plotter and the recorder on (ECP) and (S).

(16) A water quality diagnosis control is carried out based on the display of the CRT, the printer, the plotter and the recorder on (ECP) and (M).

(17) A water quality diagnosis control is carried out based on the display of the CRT, the printer, the plotter and the recorder on (ECP) and ($DH_2O_2$).

(18) A water quality diagnosis control is carried out based on the display of the CRT, the printer, the plotter and the recorder on (S) and (M).

(19) A water quality diagnosis control is carried out based on the display of the CRT, the printer, the plotter and the recorder on (S) and ($DH_2O_2$).

(20) A water quality diagnosis control is carried out based on the display of the CRT, the printer, the plotter and the recorder on (M) and ($DH_2O_2$).

(21) A water quality diagnosis control is carried out based on the display of the CRT, the printer, the plotter and the recorder on (DH), (DO) and (pH).

(22) A water quality diagnosis control is carried out based on the display of the CRT, the printer, the plotter and the recorder on (DH), (DO) and (ECP).

(23) A water quality diagnosis control is carried out based on the display of the CRT, the printer, the plotter and the recorder on (DH), (DO) and (S).

(24) A water quality diagnosis control is carried out based on the display of the CRT, the printer, the plotter and the recorder on (DH), (DO) and (M).

(25) A water quality diagnosis control is carried out based on the display of the CRT, the printer, the plotter and the recorder on (DH), (DO) and ($DH_2O_2$).

(26) A water quality diagnosis control is carried out based on the display of the CRT, the printer, the plotter and the recorder on (DH), (pH) and (SCP).

(27) A water quality diagnosis control is carried out based on the display of the CRT, the printer, the plotter and the recorder on (DH), (pH) and (S).

(28) A water quality diagnosis control is carried out based on the display of the CRT, the printer, the plotter and the recorder on (DH), (pH) and (M).

(29) A water quality diagnosis control is carried out based on the display of the CRT, the printer, the plotter and the recorder on (DH), (pH) and ($DH_2O_2$).

(30) A water quality diagnosis control is carried out based on the display of the CRT, the printer, the plotter and the recorder on (DH), (ECP) and (S).

(32) A water quality diagnosis control is carried out based on the display of the CRT, the printer, the plotter and the recorder on (DH), (ECP) and ($DH_2O_2$)

(33) A water quality diagnosis control is carried out based on the display of the CRT, the printer, the plotter and the recorder on (DH), (S) and (M).

(34) A water quality diagnosis control is carried out based on the display of the CRT, the printer, the plotter and the recorder on (DH), (S) and ($DH_2O_2$).

(35) A water quality diagnosis control is carried out based on the display of the CRT, the printer, the plotter and the recorder on (DH), (DCB) and ($DH_2O_2$).

(36) A water quality diagnosis control is carried out based on the display of the CRT, the printer, the plotter and the recorder on (DO), (pH) and (ECP).

(37) A water quality diagnosis control is carried out based on the display of the CRT, the printer, the plotter and the recorder on (DO), (pH) and (S).

(38) A water quality diagnosis control is carried out based on the display of the CRT, the printer, the plotter and the recorder on (DO), (pH) and (M).

(39) A water quality diagnosis control is carried out based on the display of the CRT, the printer, the plotter and the recorder on (DO), (pH) and ($DH_2O_2$).

(40) A water quality diagnosis control is carried out based on the display of the CRT, the printer, the plotter and the recorder on (DO), (ECP) and (S).

(41) A water quality diagnosis control is carried out based on the display of the CRT, the printer, the plotter and the recorder on (DO), (ECP) and (M).

(42) A water quality diagnosis control is carried out based on the display of the CRT, the printer, the plotter and the recorder on (DO), (ECP) and ($DH_2O_2$).

(43) A water quality diagnosis control is carried out based on the display of the CRT, the printer, the plotter and the recorder on (DO), (S) and (M).

(44) A water quality diagnosis control is carried out based on the display of the CRT, the printer, the plotter and the recorder on (DO), (S) and ($DH_2O_2$).

(45) A water quality diagnosis control is carried out based on the display of the CRT, the printer, the plotter and the recorder on (DO), (DCB) and (DH$_2$O$_2$).

(46) A water quality diagnosis control is carried out based on the display of the CRT, the printer, the plotter and the recorder on (pH), (ECP) and (S).

(47) A water quality diagnosis control is carried out based on the display of the CRT, the printer, the plotter and the recorder on (pH), (ECP) and (M).

(48) A water quality diagnosis control is carried out based on the display of the CRT, the printer, the plotter and the recorder on (pH), (ECP) and (DH$_2$O$_2$).

(49) A water quality diagnosis control is carried out based on the display of the CRT, the printer, the plotter and the recorder on (pH), (S) and (M).

(50) A water quality diagnosis control is carried out based on the display of the CRT, the printer, the plotter and the recorder on (pH), (M) and (DH$_2$O$_2$).

(51) A water quality diagnosis control is carried out based on the display of the CRT, the printer, the plotter and the recorder on (pH), (M) and (DH$_2$O$_2$).

(52) A water quality diagnosis control is carried out based on the display of the CRT, the printer, the plotter and the recorder on (ECP), (S) and (M).

(53) A water quality diagnosis control is carried out based on the display of the CRT, the printer, the plotter and the recorder on (ECP), (S) and (DH$_2$O$_2$).

(54) A water quality diagnosis control is carried out based on the display of the CRT, the printer, the plotter and the recorder on (S), (M) and (DH$_2$O,).

(55) A water quality diagnosis control is carried out based on the display of the CRT, the printer, the plotter and the recorder on time based change of the dissolved hydrogen concentration (DH) in the water quality analysis results.

(56) A water quality diagnosis control is carried out based on the display of the CRT, the printer, the plotter and the recorder on time based change of (DO) in the water quality analysis results.

(57) A water quality diagnosis control is carried out based on the display of the CRT, the printer, the plotter and the recorder on time based change of (pH) in the water quality analysis results.

(58) A water quality diagnosis control is carried out based on the display of the CRT, the printer, the plotter and the recorder on time based change of ECP.

(59) A water quality diagnosis control is carried out based on the display of the CRT, the printer, the plotter and the recorder on time based change of the solution electric conductivity in the water system.

(60) A water quality diagnosis control is carried out based on the display of the CRT, the printer, the plotter and the recorder on time based change of the measured results (M) of the DCB sensor.

(61) A water quality diagnosis control is carried out based on the display of the CRT, the printer, the plotter and the recorder on time based change of the dissolved hydrogen peroxide concentration (DH$_2$O$_2$) in the water quality analysis results.

A water quality diagnosis control may be carried out based on the display of the CRT, the printer plotter and the recorder on respective time based changes of two kinds of analyzed data. Further, a water quality diagnosis control can be carried out based on the display of the CRT, the printer, the recorder on respective time based changes of three kinds of analyzed data.

In the water quality diagnosis control, the water quality is controlled by effecting water quality analysis using a random pulse voltammetry or plural kinds of voltametries in an electrochemical cell of this invention. With the random voltammetry, a data compression method and a neural network are used. Among plural kinds of voltametries, either of pulse voltametries totaling to five kinds, in that, a reverse pulse, a normal pulse, differential pulse, a square wave and a normal differential pulse is used. Water quality is controlled by using plural kinds of voltametries or the random pulse voltammetry based on the above pattern recognition and simultaneously identifying O$_2$, H$_2$ and H$_2$O$_2$. Further, analyzed results such as on SO$_4^{2-}$, Cl$^-$ and Na$^+$ which are decomposed products of core purification resins are also displayed and compared with standard values inputted in advance to control water quality.

There is a function for controlling injection amount of N$_2$H$_4$ (hydrazin) into a steam generator based on the dissolved O$_2$ gas data in a nuclear reactor primary cooling water line. An injection amount of H$_2$ gas is controlled based on dissolved H$_2$O$_2$ data in the nuclear reactor primary cooling water line. The injection amount of H$_2$ gas may be controlled based on the measured data of H$_2$, O$_2$, and H$_2$O$_2$. An injection amount of H$_2$ gas is controlled based on dissolved H$_2$ amount in the nuclear reactor primary cooling water line. An injection amount of H$_2$ into the nuclear reactor primary cooling water is controlled based on dissolved O$_2$ gas amount in the nuclear reactor primary cooling water line. Further, an injection amount of H$_2$ gas into the nuclear reactor primary cooling water is controlled based on dissolved H$_2$O$_2$ in the nuclear reactor primary cooling water. Corrosion amount may be monitored by detecting potential of Zr alloy member of a nuclear fuel assembly in a nuclear power plant.

DETAILED DESCRIPTION OF THE PREFERRED EMBODIMENTS

Embodiment 1

Figure 2:
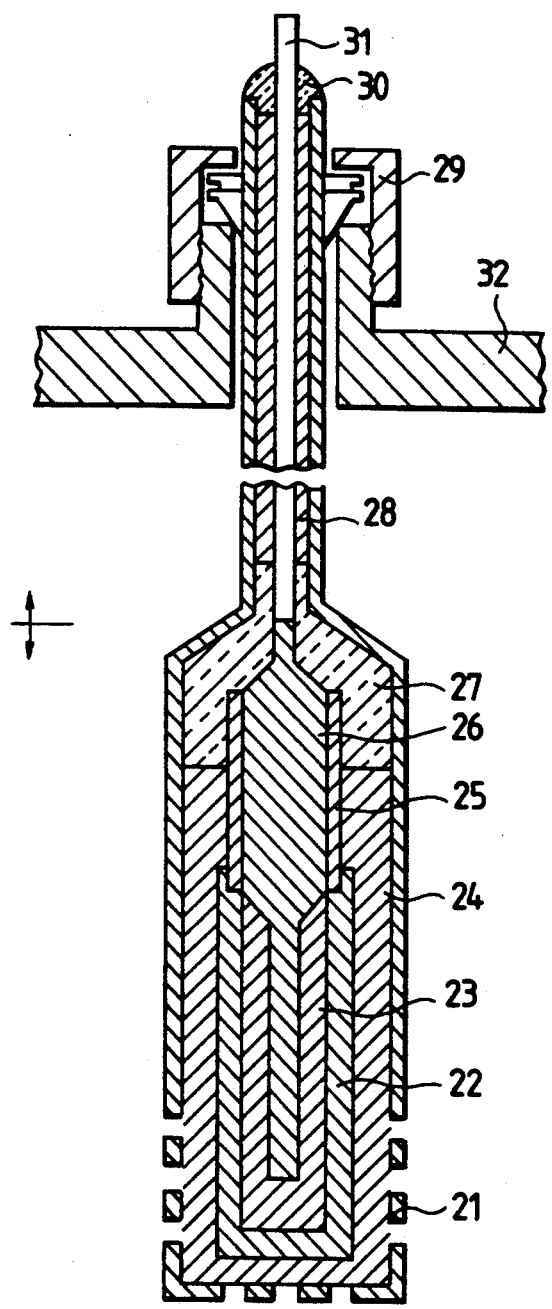
FIG. 2 is a cross sectional view illustrating one structure of a halogenated inner reference electrode.

The present embodiment is an example wherein the water quality control in a nuclear reactor was tried by disposing the ECP sensor as shown in FIG. 2 in the nuclear reactor of a BWR plant as shown in FIG. 1 through an instrumentation piping in the nuclear reactor and by measuring a time based change in corrosion potential of the reactor structural material under this water quality environment with reference to the potential of the ECP sensor (corresponds to the reaction of AgCl+e→Ag+Cl$^-$ et al.) In FIG. 1, the ECP sensor 2 is inserted in a reactor instrumentation piping 4 of a core 3 in a nuclear reactor pressure vessel 12. 1 is a drier, 5 is a potentionstat of electrochemical interface, 6 is a computerized arithmetic processing automatic control unit, 7 is a remote control command unit and an analysis result display and output unit, 8 is a gas and chemical injection line, 9 is a turbine, 10 is a nuclear reactor water supply pipe and 11 is a nuclear reactor recirculation line. FIG. 2 shows the constitution of the ECP sensor according to the present invention. The present silver/halogenated silver electrode does not at all include a solution layer containing such as KCl a its constitutional element.

In the drawing, both faces of silver wire 26 are coated with alumina or zirconia through a CVD method, on the portion not formed of the ceramic coating halogenated silver (AgCl, AgBr or AgI) 23 is adhered. After adhering the halogenated silver, alumina coating 22 having thickness of several hundreds μm and porosity ratio of below 70% is formed on the surface through such as electrophoresis method. Further, around its periphery alumina coating 24 having thickness of a few mm and porosity ratio of below 10% is formed through such as plasma spray method or compression forming. In case halogenated silver is not used, a structure of silver wire 26 directly coated with ceramics layers 24 and 25 is able to function as an ECP sensor of $Ag/Ag^+$.

The sensor portion thus constructed is enclosed by a SUS316L guard 21 provided with a small aperture at its bottom to safeguard the sensor portion. The one end of the silver wire 26 is electrically connected to a lead wire 31 made of SUS316L. The top of the sensor portion is sealed with glass 27. Further, the space between the guard 21 and the lead wire 31 is filled with magnesia 28 to isolate the both and the ends thereof are sealed with glass 30.

This sensor is fixed at a fixing member 29 in the instrumentation piping and the sensor signals are taken out to the outside through a cable 32. With the sensor thus constituted, the high temperature water of the plant does not contact directly to the solid electrolyte (halogenated silver) so that extremely long life time is achieved. Accordingly, the sensor is disposed in the high temperature water of the plant during the period from one inspection to the next inspection of the plant and direct data with respect to water quality are continuously obtained so that the credibility of the data extremely increases.

Figure 3:
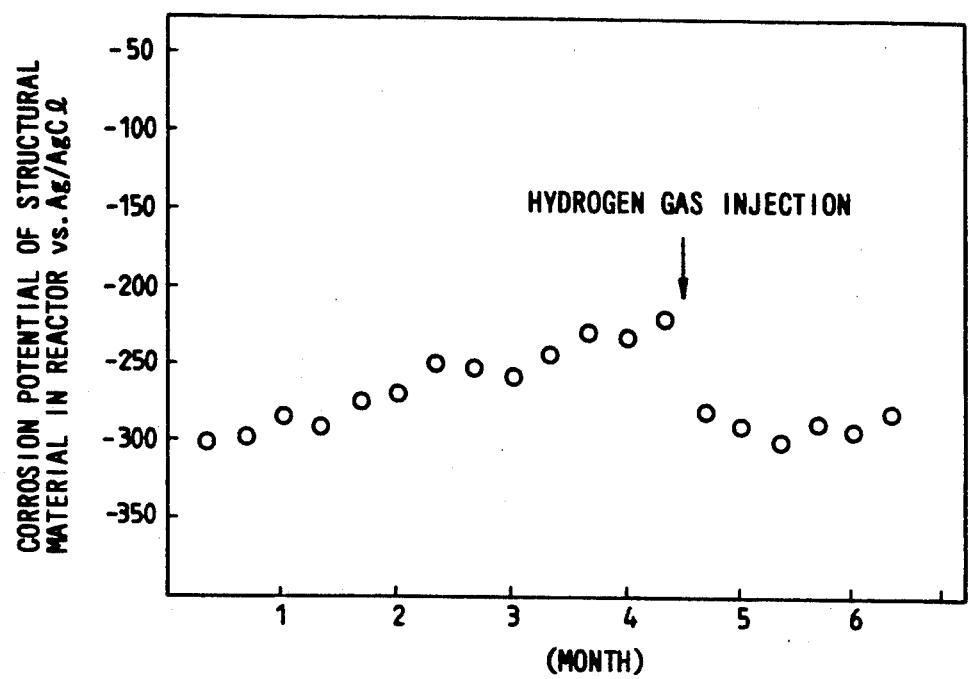
FIG. 3 is a graph illustrating a relationship between the time based change of corrosion potential of a structural material in the reactor and the hydrogen gas injection effect.

FIG. 3 illustrates corrosion potential with respect to time of the reactor structural member by using the ECP sensor which is outputted to the analysis result display system (cathode ray tube display system) 7 of FIG. 1. When hydrogen gas is injected from the gas injection line 8, the corrosion potential of the reactor structural material decreases with good response which proves that the water quality diagnosis central system is sufficiently useful for the corrosion suppression.

Figure 4:
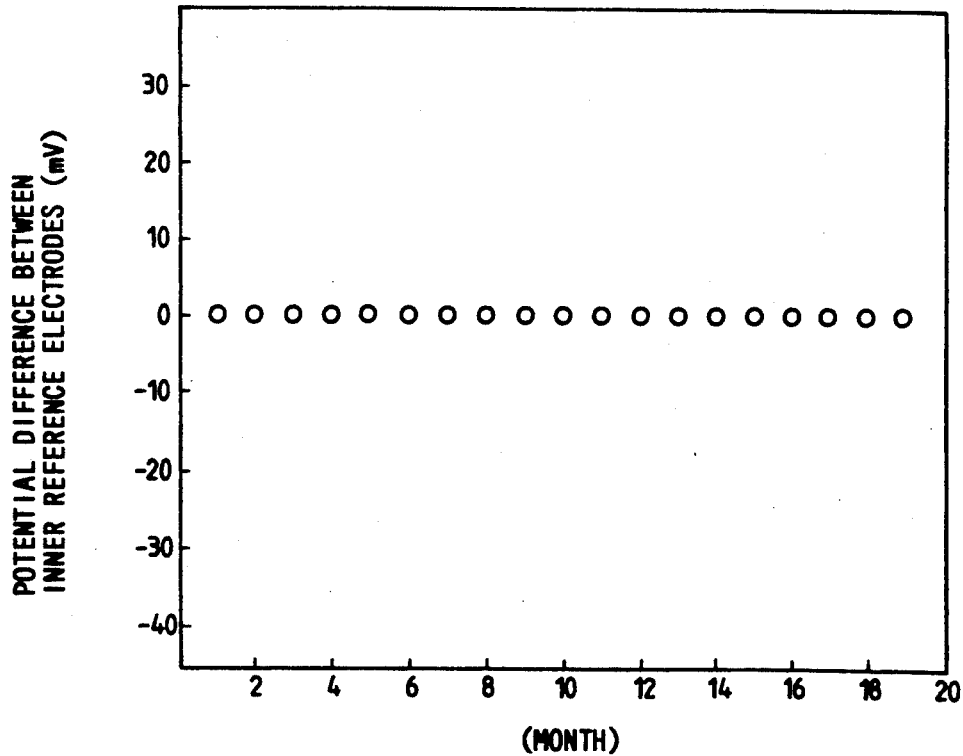
FIG. 4 is a graph illustrating the potential difference between the halogenated inner reference electrodes.

As shown in FIG. 4, no potential difference with another identical ECP sensor installed in the reactor instrumentation piping appears on the display system 7 for a long time, which proves that this ECP meter has an excellent stability and durability.

Embodiment 2

The present embodiment shows an example wherein a hydrogen ion concentration meter has been installed in the reactor instrumentation piping shown in FIG. 1. By measuring the potential of this hydrogen ion concentration meter in comparison with potential of the ECP sensor providing the reference potential shown in FIG. 2, a potential output is obtained corresponding to hydrogen ion concentration of the solution. The constitution of the hydrogen ion concentration meter used here is the same as that shown in FIG. 2 except that metal oxide $Pt/Tl_2O_3$, $Ag/Ag_2O$, $Hg/Hg_2O$, $Cu/Cu_2O$, $Cu/CuO$, $Ir/Ir_2O_3$ or $Ir/IrO_2$) is used in place of the halogenated silver in FIG. 2.

Figure 5:
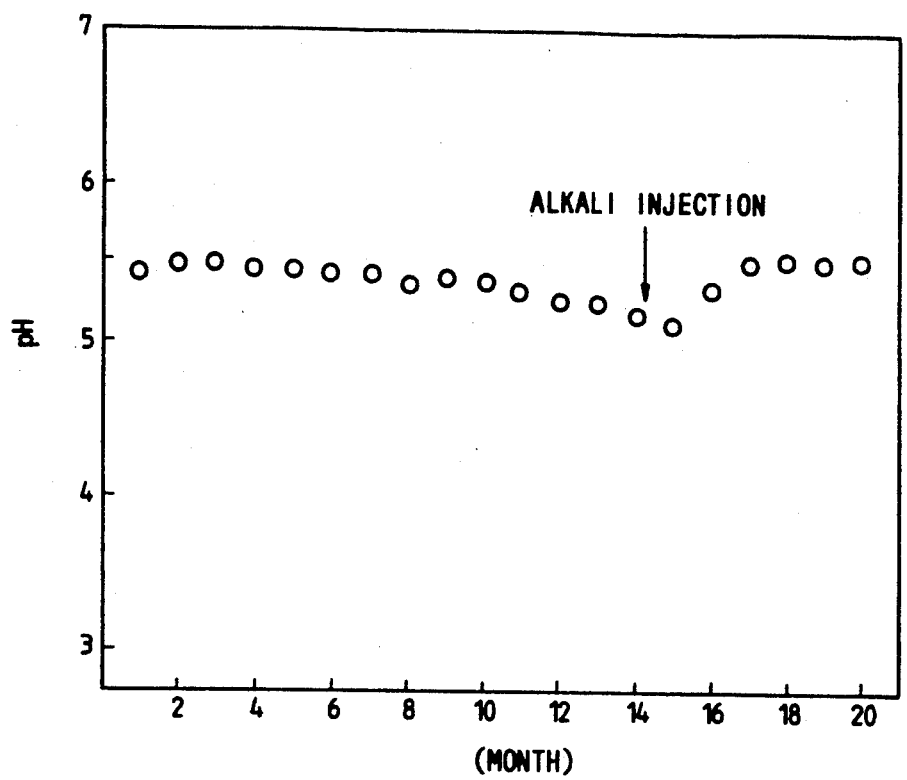
FIG. 5 is a graph illustrating a relationship between the time based pH change in the reactor and the alkali injection effect.

FIG. 5 shows a time based change of pH (logarithm of ion concentration of hydrogen). When a slight amount of alkali is injected from the injection system 8 during a slight fall of pH in FIG. 5 outputted on the display system, the pH in the reactor begins to rise after a predetermined interval which shows that the water quality diagnosis control is carried out sufficiently.

Embodiment 3

Figure 6:
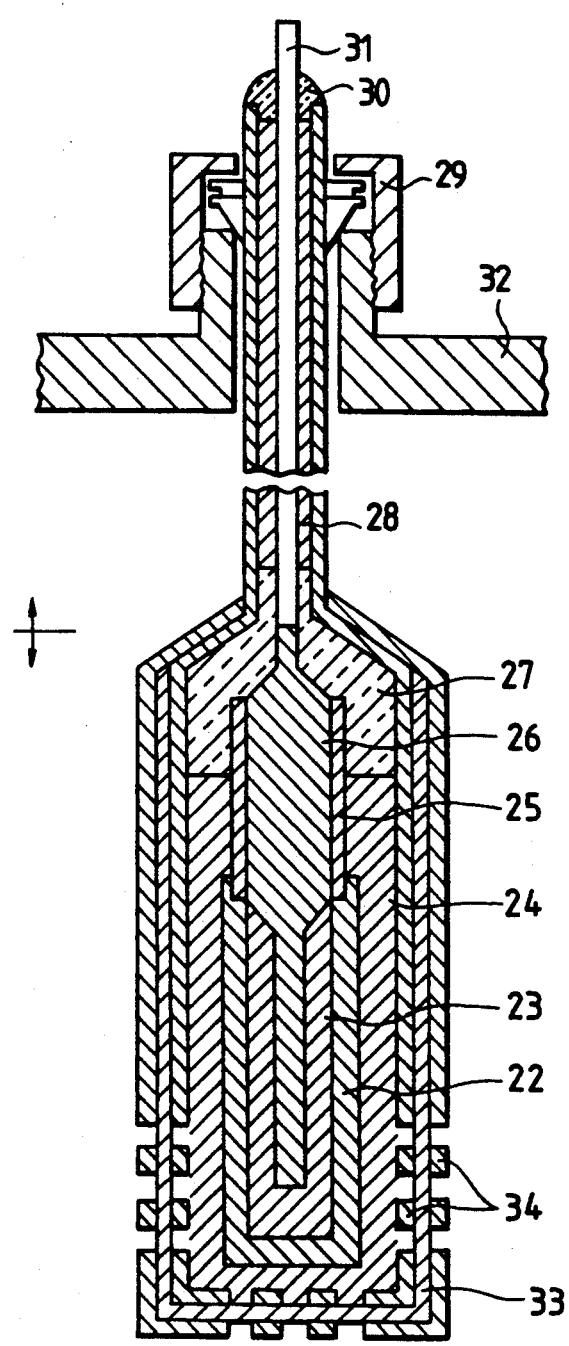
FIG. 6 is a cross sectional view illustrating another structure of a hologenated inner reference electrode.

The present embodiment like the embodiment 2 monitors the water quality environment in the reactor by simultaneously inserting an inner reference electrode and a pH sensor in the reactor instrumentation piping. The structure of the inner reference electrode used here is fundamentally the same as that shown in FIG. 2 except that the ceramic layer of the SUS316L guard and its inner liner is double-structured. Its structure is shown in FIG. 6. In the drawing, the portion different from FIG. 2 is that the coating such as alumina and zirconia is sandwiched by the SUS316L guard. Further, the pH electrode used in this embodiment also uses the double-structured guard as shown in FIG. 6.

Figure 7:
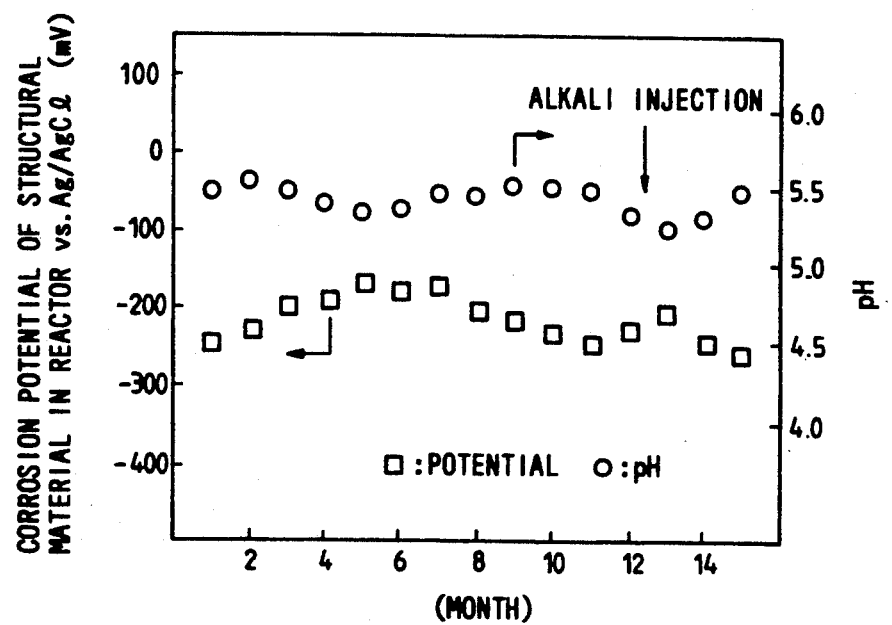
FIG. 7 is a graph illustrating a relationship between the corrosion potential of a structural material in the reactor and the chemical injection effect.

On the display system 7 relationship between corrosion potential of the reactor structural material in FIG. 7 and pH is displayed, and generally there appears a tendency for the corrosion potential of the structural material rising during fall of pH.

When alkali is injected from the chemical injection system 8, there appears a clear tendency of falling in corrosion potential and of rising in pH so that a sufficient increase in corrosion resistance of the reactor structural material is effected through the water quality diagnosis control.

Embodiment 4

Figure 8:
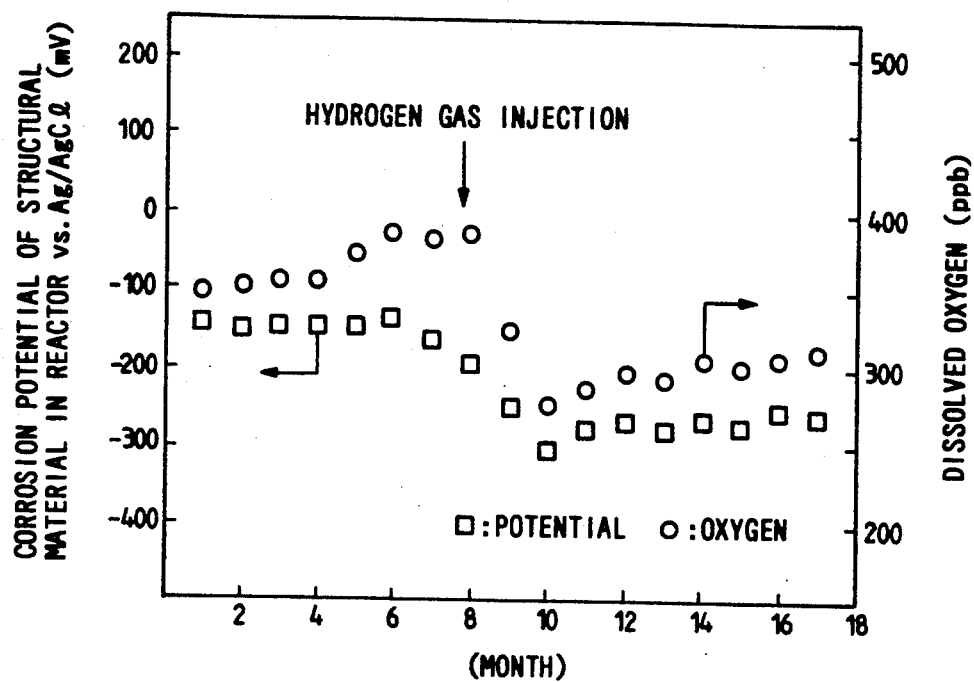
FIG. 8 is a graph illustrating a relationship among the corrosion potential of a structural material in the reactor, the time based change of the dissolved oxygen concentration, and hydrogen gas injection effect.
Figure 16:
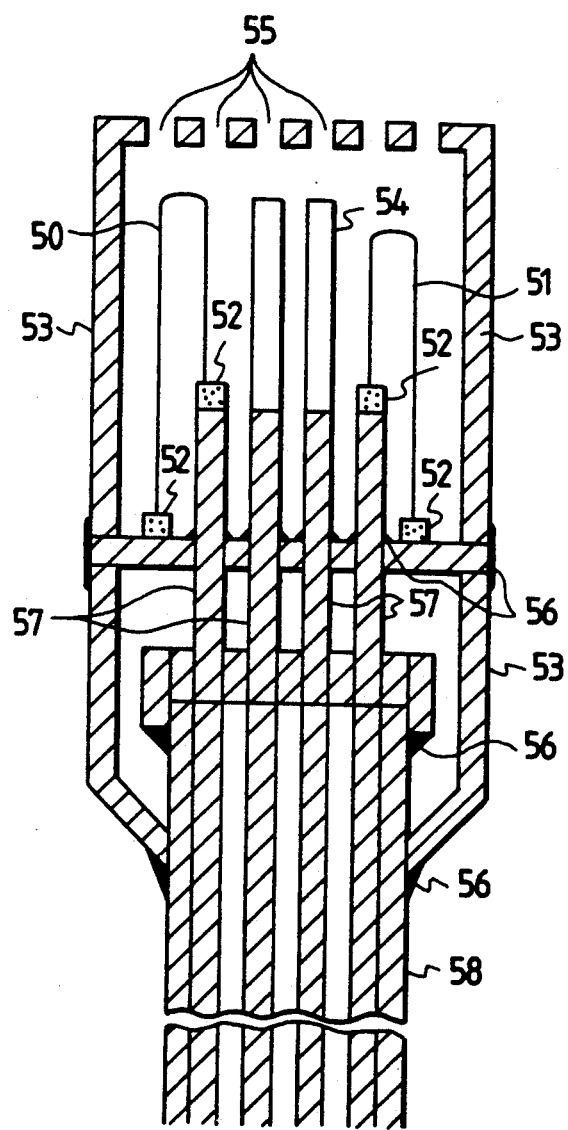
FIG. 16 is a cross-sectional structure of an electrochemical sensor comprising an internal reference electrode, a work electrode, a counter electrode, and a pH electrode.

In the present embodiment, an electrochemical measuring system integrating a micro platinum electrode 50 as shown in FIG. 16 as sensors of dissolved oxygen, hydrogen and hydrogen peroxide and the inner reference electrode as shown in FIG. 2 and FIG. 6 is installed in the reactor instrumentation piping 4. In FIG. 8, the micro platinum electrode is used as the dissolved oxygen meter making use of electrochemical measurement and measures and displays the dissolved oxygen concentration around the periphery of the reactor as well the time based change of the corrosion potential of the reactor material. Through the hydrogen gas injection from the gas injection system 8 the dissolved oxygen concentration falls and the corrosion potential also decreases which shows that sufficient water quality diagnosis control is effected.

The analysis method of dissolved hydrogen, oxygen and hydrogen peroxide in the reactor using the plural kinds of voltametries carried out in this embodiment, and the following embodiment is performed with the following sequence.

Figure 17:
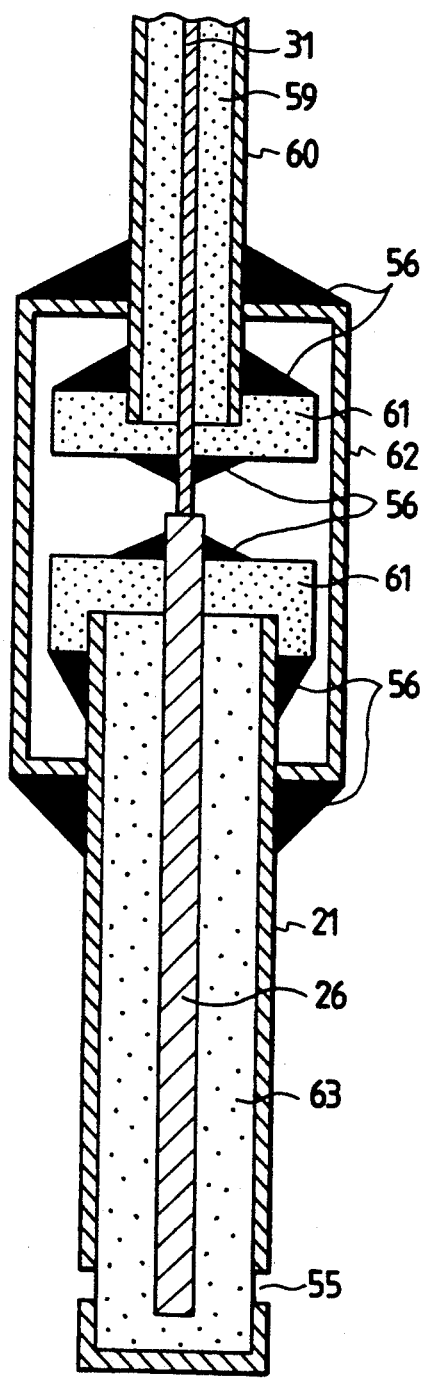
FIG. 17 a cross-sectional view in detail of a ceramic internal silver/silver ion reference electrode.

By using a normal pulse voltammetry and a reverse pulse voltammetry as the plural kinds of voltammetries in the present embodiment separation and determination of the dissolved hydrogen, dissolved oxygen and dissolved hydrogen peroxide is carried out. In the case where the inner reference electrode (ECP sensor) or the present invention a shown in FIG. 2 or in FIG. 17 is used as the reference electrode and the counter electrode for electrochemical measurement, and the micro platinum disk electrode is used as the working electrode, the total diffusion limiting currents in oxidation and reduction of the solution including DH, DO, and $DH_2O_2$ are expressed by the following equations with regard to the respective modes of the normal pulse voltammetry and the reverse pulse voltammetry.

$$I^p_{i,N} = \sum_j i_{ss} f[P(t_p)]_j, \, j = H_2O_2, O_2 \tag{1}$$

-continued $$I^A_{l,Np} = -\sum_j iss[f(P(tp))]_j, j = H_2O_2, H_2 \quad (2)$$

$$I^A_{l,Rp} = -\sum_j iss[f(P(\tau))]_j, j = H_2O_2, H_2 \quad (3)$$

$$I^c_{l,Rp} = iss_{(O2)}[f(P(tp))]_{(O2)} - iss_{(H2O2)}[f(P(\tau))]_{(H2O2)} + \quad (4)$$

$$2iss_{(H2O2)}\{[f(P(tp))]_{(H2O2)} - f(P(\tau))]_{(H2O2)}\}$$

Wherein $I^c_{l,Np}$ and $I^A_{l,Np}$, in the equations (1) and (2) are respectively the total diffusion limiting current for the reduction reaction of $H_2O_2$ and $O_2$, and the total diffusion limiting current for the oxidation reaction of $H_2O_2$ and $H_2$ in the normal pulse voltammetry. $I^A_{l,Rp}$, and $I^c_{l,Rp}$ respectively show the total diffusion limiting current for the oxidation reaction of $H_2O_2$ and $H_2$ and the total diffusion limiting current for the reduction reaction of $H_2O_2$ and $O_2$ in the reverse pulse voltammetry.

$$f(P) = \sqrt{\pi/4P} + \pi/4 + 0.094\sqrt{P} \quad (5)$$

Wherein $p=4Djtp/r^2$, D is a diffusion coefficient of respective reaction species j, tp is pulse width of the normal pulse and the reverse pulse, and r is radius of the micro disk electrode. $\tau$ in equations (3) and (4) is retention time of the initially set potential of the reverse pulse voltammetry, in other words, the so-called generation time. The equation (5) is valid upto the radius of the micro electrode $r=50\mu m$ and tp and $\tau$ are about 600 ms. iss indicates a steady current at to micro electrode and is expressed as iss $=4nFDjrC°j$, wherein, n shows total reaction electron numbers of the respective oxidation and reduction reaction with regard to oxygen, hydrogen, and hydrogen peroxide, F is the Faraday constant, and C°j is concentration of respective chemical species j.

Here, when $I^c_{l,Np}$ of equation (1) iss subtracted from $I^c_{l,Rp}$ of equation (2), the following equation is obtained;

$$I^c_{l,Rp} - I^c_{l,Np} = \tau(tp,\tau) \cdot 8C° (H_2O_2)^{FrD}(H_2O_2) \quad (6)$$

by indicating $I^C_{l,Rp} - I^c_{l,Np}$ on ordinate and $\xi(tp,\tau)$ on abscissa and determining and plotting $\xi(tp,\tau)$ for several pulse widths of the normal pulse and the reverse pulse, C° ($H_2O_2$), in that, hydrogen peroxide concentration, is obtained by calculation from the inclination of its straight line. The diffusion coefficient D($H_2O_2$) of hydrogen peroxide is determined in the laboratory before hand. Wherein, $$\xi(tp, \tau) = \sqrt{\pi r} \ (1/\sqrt{tp} - 1/\sqrt{\tau})/4 \sqrt{D} +$$

$$0.188 \sqrt{D} \ (\sqrt{tp} - \sqrt{\tau})/r$$

Herein, once hydrogen peroxide is separated and determined with the sequence shown in the equation (6), the remaining hydrogen concentration C° $H_2$ is determined by substituting C° ($H_2O_2$) in the equations (2) and (3). Further, when substituting C° ($H_2O_2$) in the equation (1) the oxygen concentration C° $O_2$ is determined. All of the above arithmetic processing is programmed in advance in the arithmetic processing automatic control device of computer 6 and is automatically carried out.

Figure 9:
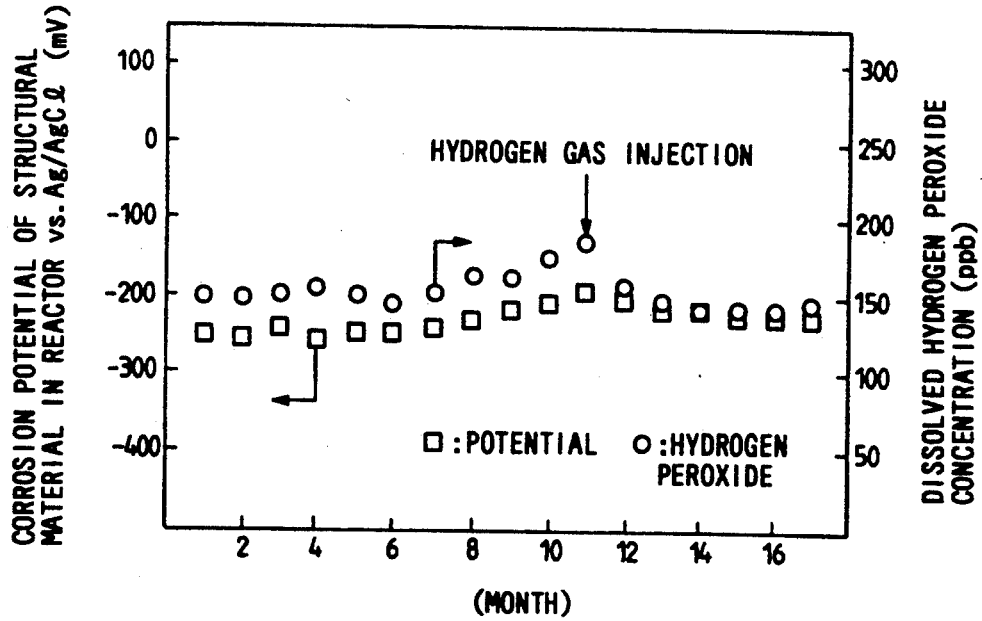
FIG. 9 is a graph illustrating a relationship among the corrosion potential of structural material in the reactor, the time based change of dissolved hydrogen peroxide concentration and chemical injection effect.
Figure 10:
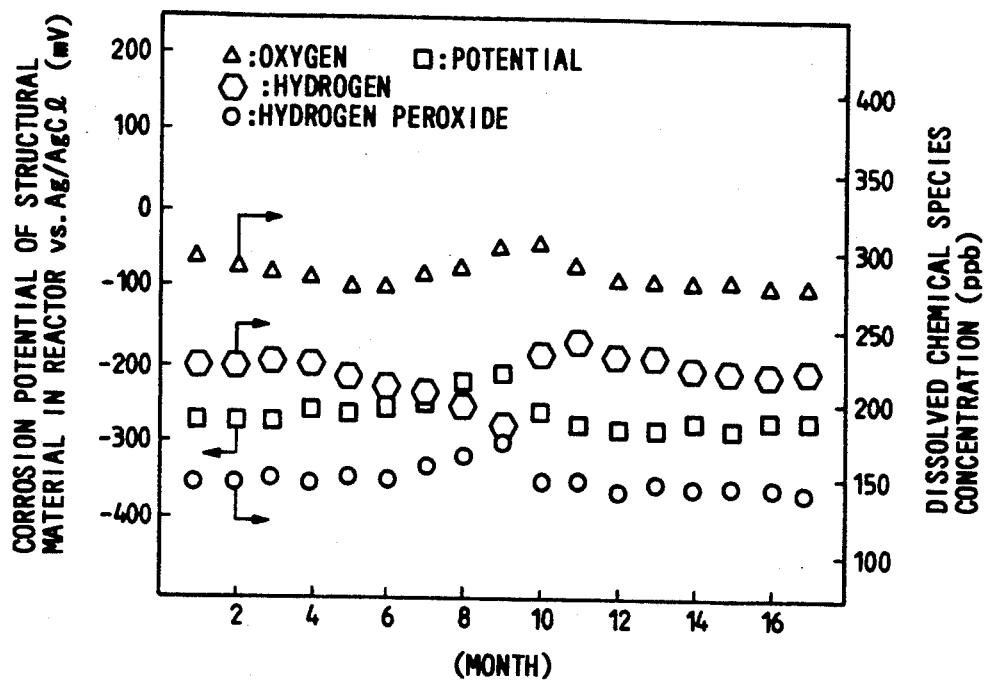
FIG. 10 is a graph illustrating a relationship among the corrosion potential of a structural material in the reactor, the time based change of dissolved oxygen, hydrogen, and hydrogen peroxide concentrations, and chemical injection effect.

The measurement results shown in FIG. 8, FIG. 9 and FIG. 10 are ones displayed by using the analysis sequence indicated in the present embodiment.

According to the present invention, direct data relating to the high temperature water in the plant is sampled so that data credibility is extremely increased, and further direct data of the high temperature water to be monitored is continuously sampled so that the accuracy of the plant operating condition monitoring is enhanced.

Embodiment 5

The present embodiment uses the micro platinum electrode in the reactor instrumentation piping 4 as the hydrogen peroxide sensor and measures in-situ the hydrogen peroxide concentration in and near the reactor through the electrochemical measurement system as structured in FIG. 16 by using the inner reference electrode as shown in FIG. 2, FIG. 6 and FIG. 17. When hydrogen gas is injected from the injection system under the computer control during the slight rise of hydrogen peroxide concentration as shown in FIG. 9, an apparent fall of hydrogen peroxide concentration is observed at the display system and accompanying thereto the corrosion potential tends to decrease slightly. Since this hydrogen peroxide can not discriminate from the dissolved oxygen and hydrogen through the usual electrochemical analysis, they were separated and determined by performing plural kinds of pulse voltammetries and arithmetic processing.

Embodiment 6

Figure 11:
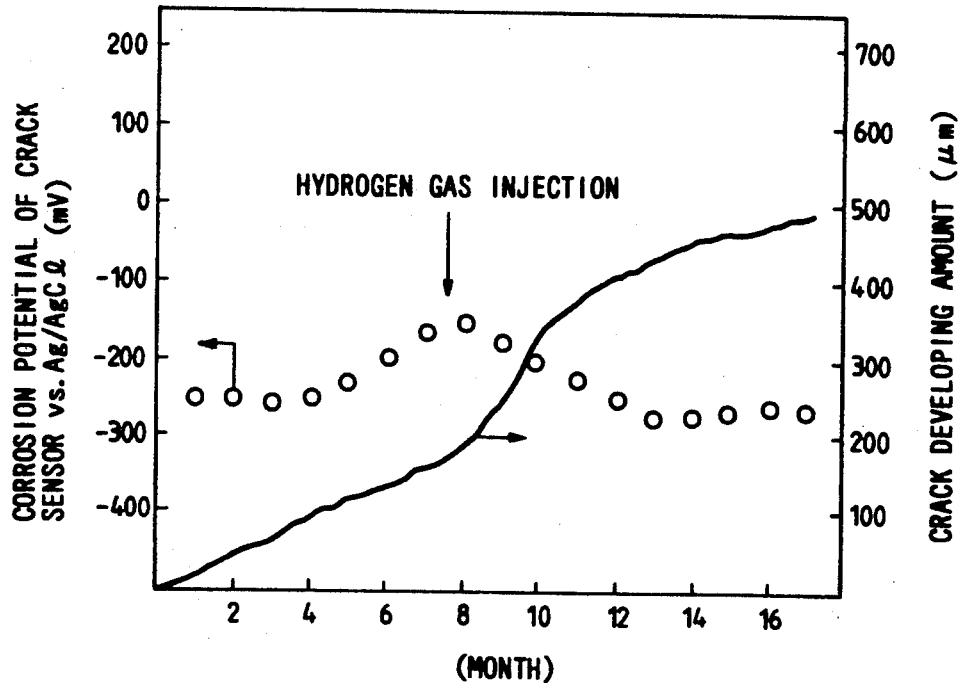
FIG. 11 is a graph illustrating a relationship among the corrosion potential of a crack sensor, the time based change of the crack developing amount of the sensor, and chemical injection effect.

In the present embodiment, the crack sensor is installed in the reactor instrumentation piping 4, the inner reference electrode (ECP sensor) as shown in FIG. 2 and FIG. 6 is jointly used, and a relationship between the crack development amount of the SUS304 steel in the reactor water environment and its corrosion potential is observed at the display system. As shown in FIG. 11, the corrosion potential and the crack development amount due to stress corrosion cracks (SCC) are correlated and it is understood that the development speed is high in the period when the corrosion potential is high. By injecting hydrogen gas through the gas injection system 8 the crack development amount tends to slightly decrease. Thereby, it is understood that a sufficient water quality diagnosis control is carried out.

Embodiment 7

Figure 12:
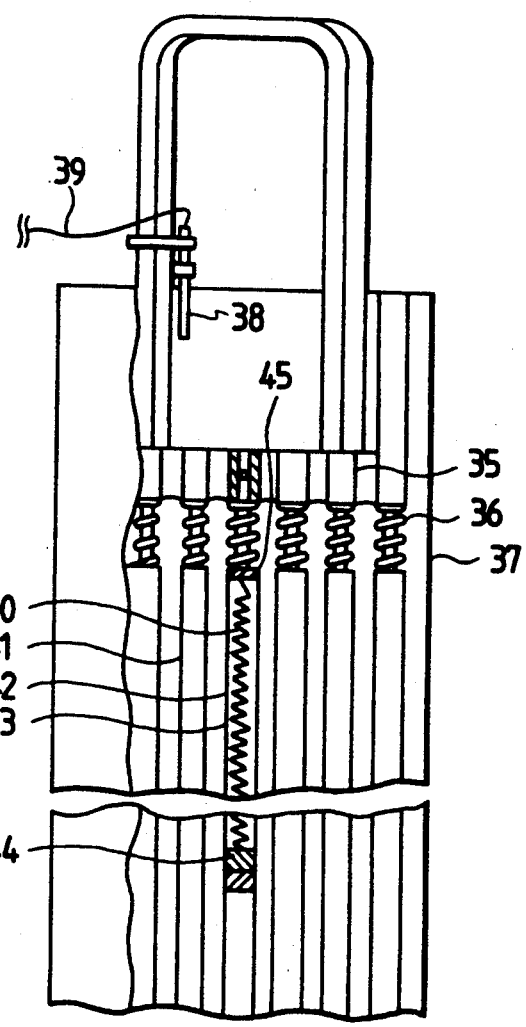
FIG. 12 is a partial cross sectional view illustrating a structure of a nuclear fuel assembly applied of the present invention.

In the present embodiment, near the fuel assembly as shown in FIG. 12 the inner reference electrode (ECP sensor) as shown in FIG. 2 is disposed. In FIG. 12, uranium pellets 44 are filled into a fuel cladding tube 42 made of Zr alloy and fixed by a fuel holding means 40 and an end plug 45 to constitute a fuel element 41. In a channel box 37, many elements are gathered and held by bolts 36 and spacers (not shown) to constitute the fuel assembly. A sensor 38 is, for example, fixed at the upper tie-plate and the water quality data is taken out through a cable 39.

Figure 13:
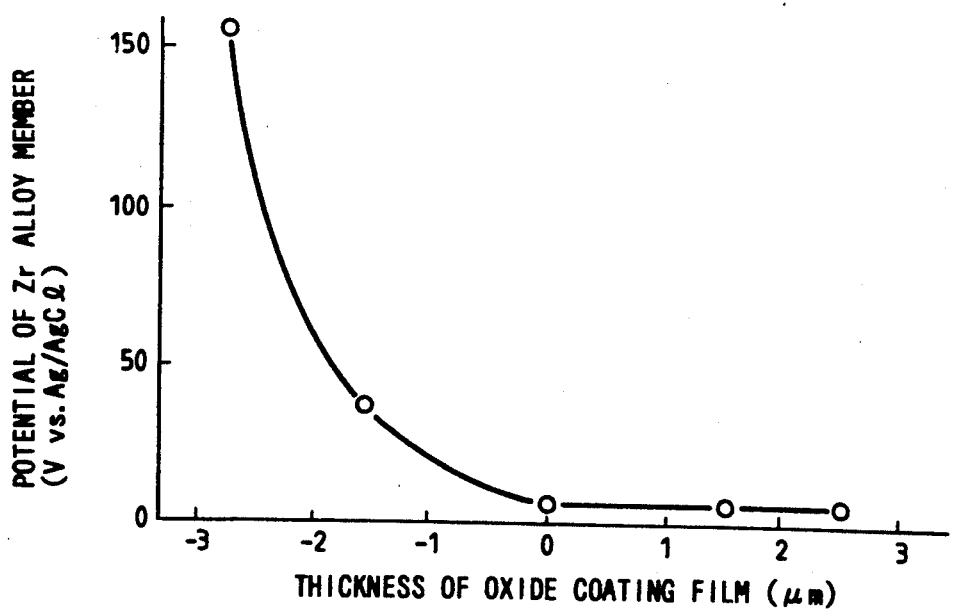
FIG. 13 is a graph illustrating a relationship between the corrosion potential of a fuel cladding tube made of Zr alloy and the thickness of the oxide coating film of the Zr alloy, and, FIG. 14 and FIG. 15 are flowcharts in plant operating conditions monitoring system of the present invention.

This embodiment is an example of monitoring the oxide coating thickness of the Zr alloy material by measuring the corrosion potential of the fuel cladding tube made of Zr alloy. Since laboratory data on the relationship between the corrosion potential of the Zr alloy member and the oxide coating thickness are inputted in advance, based on its reference value the oxide coating thickness of the cladding tube is immediately determined from the measurement results of the corrosion potential by using the display system 7. The results are illustrated in FIG. 13.

Embodiment 8

Figure 14:
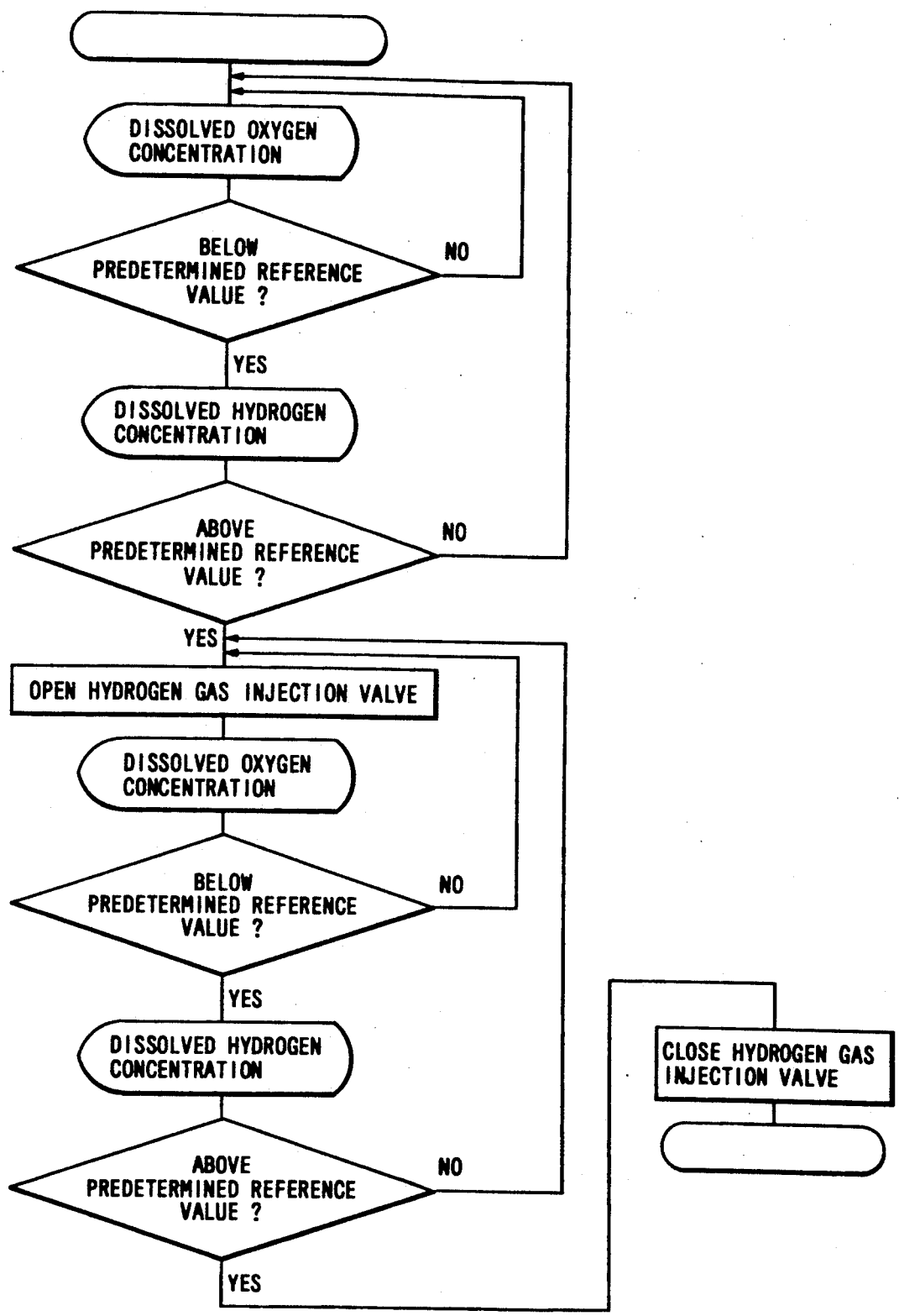

FIG. 14 is a flow chart of a continuous water quality control during continuous monitoring of dissolved oxygen and hydrogen in the reactor water by installing the electrochemical measurement system shown in FIG. 16 into the instrument tube in the reactor. When the dissolved oxygen concentration in the nuclear reactor water exceeds a predetermined reference value, the relationship in the amount of difference of the dissolved oxygen concentration with the predetermined reference value is determined, and when both the dissolved oxygen and the dissolved hydrogen concentration exceed over the predetermined values, the hydrogen gas injection is started through the gas and chemical injection line 8 by opening the hydrogen gas injection valve. Thereafter, the relationship in the difference amounts of the dissolved oxygen and hydrogen concentration is again determined, and the hydrogen gas injection is continued until the conditions are satisfied that the dissolved oxygen concentration be lower and the dissolved hydrogen concentration be higher than the predetermined values.

Embodiment 9

In this embodiment, the electrochemical measurement system shown in FIG. 16 is installed in the instrumentation tube in the nuclear reactor, where the pH sensor having the structure as shown in FIG. 2 is used, wherein platinum wire instead of silver wire 26, and thallic oxide instead of halogenated silver 23 are used. FIG. 16 shows a treatment flow chart for continuously monitoring pH in the reactor water and maintaining the pH of the reactor water within a predetermined range by injecting weak acid and weak alkali. The weak alkali injection is performed when the pH is below the predetermined range and the weak acid injection is performed when the pH is above the predetermined range.

Embodiment 9

An electrochemical analysis system shown in FIG. 16 has been installed in an instrumentation tube in a nuclear reactor. Here, actually, a pH sensor with the structure as shown in FIG. 2 has been used, wherein a platinum wire instead of a silver wire 26, and a thallic oxide instead of a halogenated silver 23 are used.

Figure 15:
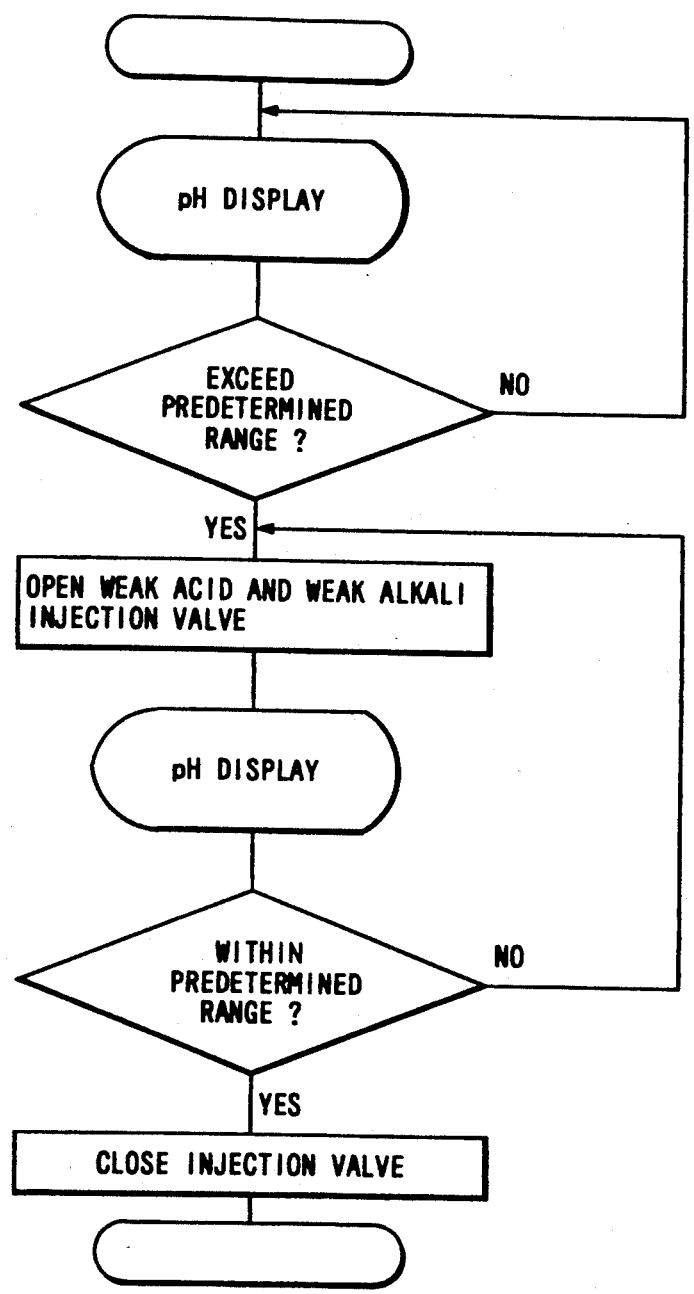

FIG. 15 shows a treatment flow chart for continuously monitoring pH in the reactor water and maintaining the pH of the reactor water within a predetermined range by injecting weak acid and weak alkali. The weak alkali injection is performed when pH is below the predetermined range and the weak acid injection is performed when the pH is above the predetermined range.

Embodiment 10

FIG. 16 is a cross sectional view of an electrochemical cell in a neutron instrumentation tube. In this embodiment, a micro platinum wire of 20 $\mu$m diameter is used as a working electrode. A case 53 encasing respective electrodes of the electrochemical cell is made of SUS316 steel. On the top of the case 53 are communication apertures permitting passage of the cooling water in the reactor and the liquid therein. The apertures facilitate gathering information regarding the cooling water in the reactor, minimizing fluctuations in electrochemical analysis, measurements of pH and corrosion potentials due to convection in the electrochemical cell caused by an inflow of incore water.

Numeral 2 indicates a low impedance silver/silver ion reference electrode. Numeral 50 shows a working electrode in U form made of platinum wire of 20 $\mu$m diameter. Numeral a platinum/thallic oxide ($Tl_2O_3$) pH electrode, potential thereof corresponds to the concentration of hydrogen ion in the reactor water. 51 shows a counter electrode made of platinum wire of 50 $\mu$m. 52 is a sealing member for preventing decreases in insulation resistance in the sheath and a core wiring of a mineral insulator (MI) cable 57 due to a leakage of incore water at the time of connecting the core wire and the counter electrode by metalizing aluminum oxide ($Al_2O_3$) with tungsten. 52 of the working electrode 50 has the same function.

Numeral 56 indicates welded portions. As is clear from this figure, although the reactor water directly permeates into the upper portion of the cell vessel through the apertures 55, the same is unable to permeate into the lower space confronted by a separation structure.

The four MI cables in the lower space being plugged in the metal tube 58 and taken out of the reactor through the instrumentation tube, are connected to a computer by means of a ordinary interface technology through a potentiostat, and function-generator 5 as shown in FIG. 1. Variety of electrochemical measurements such as pulse voltammetry, random pulse voltammetry and the like are possible to be performed. Further by connecting a lead wire with the structure member which is short-circuited to the welds 56 and the metal tube 58, and by measuring the difference in potential between 2 and the same by using an electrometer, a corrosion potential of the stainless steel under the environment of the water quality of a reactor is possible to be measured.

Further by connecting the electrometer between 2 and 54, reference potential of the electrode 54, reference electrode of 2, is able to be measured. Thereby, by measuring the difference in potential between 2 and 54 pH of the reactor water is obtained. In order to satisfy the requirement for compactness so as to be installed in a neutron instrumentation, and to reduce impedance due to the resistance of the cell and the like during measurement in high temperature and high pressure water with low electrical conductivity, the four electrodes of 2, 50, 54 and 51 are disposed in close proximity. The inner cell diameter of the vessel 53 filled with reactor water is 20 mm. The four electrodes are disposed in a circular arrangement in the cell as close as possible.

FIG. 17 is an enlarged view in detail of the reference electrode 2 shown in FIG. 16. This electrode is composed of a silver/silver ion electrode. The aluminum oxide porous layer 63 surrounding the silver wire 26 is composed of a compression moulded powdered aluminum oxide (300 mesh pass). The porous layer 63 is filled with reactor water passing through an aperture 55 with about 0.5 mm diameter, and stores silver ion dissolving from the silver wire. A diffusion speed of silver ion diffusing from the compression moulded layer 63 into the reactor water through the liquid communication aperture 55, varies depending on compression pressure applied on the mould. By adjusting compression pressure, the diffusion speed has been controlled to be under $10^{-12}$ mol/cm$^2$·s.

21 is a sheath of the silver/silver ion electrode. 61 is a seal made of tungsten metallized alumina for prevention of decrease in insulation resistance due to a leakage of reactor water. 59 is an aluminum insulation layer. 31 is an MI cable of SUS304 serving as a lead wire for the silver wire 26. 60 is a sheath of the MI cable, made of the same SUS304 as the cable. 62 is an adapter for connecting the MI cable with the electrode member.

Embodiment 11

In this example embodying the present invention, by using an electrochemical sensor as shown in FIG. 16, and installing the same in place of the ECP sensor in FIG. 1, and further by applying a random pulse voltammetry and a neural network, concentrations of dissolved oxygen, hydrogen peroxide and hydrogen ($C^*(O_2)$, $C^*(H_2O)$, $C^*(H_2)$) are analysed quantitatively and simultaneously.

The random pulse voltammetry is a volammetry thereto the pattern recognition method is applied. In the voltammetry shown in the embodiment 4 wherein a normal pulse and a reverse pulse are used in combination, measurement of concentration of each chemical species depends on variable one-dimensional information on a diffusion limiting current. In this embodiment, however, by fluctuating a system to measure in multi-modes with more complicated fluctuation signals (random pulse potential signals), an attempt to obtain as much of electrolytic current data (pattern information) as possible including information on electro nosp chemical reactions of each system to measure has been made. Namely, even with such chemical species as the above wherein response potentials between them are very close and difficult to separate for measurement, by focusing on their characteristic patterns or characteristic vectors obtained, by means of a data compression processing explained below, based on the differences in the speed of their charge transfer, parameters and the like among other electrochemical reaction processes, their quantitative and qualitative analyses are obtained, the former from a size and a measured line of a characteristic vector, the latter from the difference in appearance patterns of a characteristic vector.

The random pulse voltammetry is executed in order of (1) gathering pattern information (electrolysis current data), (2) compression of pattern data, (3) extraction of object information from compressed pattern information $C^*(O_2)$, $C^*(H_2O_2)$, $C^*(H_2)$ values. The outline of each step of (1), (2) and (3) is as follows. In step (1), electrolysis currents of oxygen, hydrogen peroxide and hydrogen are measured as response signals corresponding to random pulse potential inputted to a measuring system. In this embodiment, a potential signal of a random pulse is expressed by using two potential waveform parameter (m,n), namely, a potential corresponding to the pulse potential of the first random pulse is represented by m, and another one corresponding to the pulse potential of the second random pulse is expressed by n. Therefore, by taking m on the x axis, and n on the y axis, electrolysis currents, i.e., response signals responding to each input potential on the (x,y) coordinates, are measured and arranged in form of a matrix corresponding to the values of parameters. In step (2), a data matrix consisting of 64 (8×8) points representing the current component of a response signal obtained in step (1) corresponding to an input potential signal is transformed and compressed into data vectors with several components. As means for data compression, there are Hadamard transformation, Karhunen-Loéve transformation, Haar transformation and the like used in Fourier transformation or in image processing. In this embodiment, the two-dimensional Hadamard transformation is used. In step (3), by extracting characteristic vectors from the data vectors obtained in step (2), $C^*(O_2)$, $C^*(H_2O_2)$, $C^*(H_2)$, are determined. That is, through entering each component from the obtained data vectors, functions capable of outputting corresponding $C^*(O_2)$, $C^*(H_2O_2)$, $C^*(H_2)$ are sought, and set up. In this embodiment, the function is determined by using a neural network. Each step of (1), (2) and (3) in this embodiment is explained below in detail.

First, "gathering of pattern information" in step (1) is explained in detail.

Figure 18A:
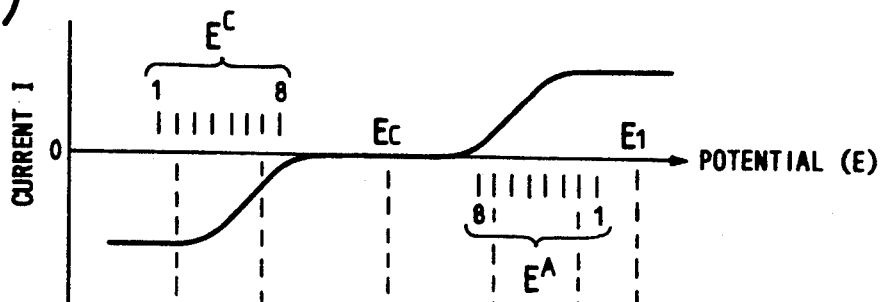
FIG. 18($a$) shows a curve of current (i)-potential (E) for a system of a three species mixture of oxygen, hydrogen peroxide and hydrogen.

FIG. 18 explains a method for applying a random pulse potential signal. Nevertheless, simply applying random pulse potential signals sometimes fails to give information on $C^*(O_2)$, $C^*(H_2O_2)$, $C^*(H_2)$. Considering that the voltammetry as described in the embodiment 4 using a normal pulse and a reverse pulse in combination has been capable of separating and determining $C^*(O_2)$, $C^*(H_2O_2)$, $C^*(H_2)$, a random pulse potential signal method based on the above combined pulse application method has been devised in this embodiment. FIG. 18 is a schematic diagram showing a current (i)-potential (E) curve in a three species mixture system of oxygen, hydrogen peroxide and hydrogen. In the positive region of potential, oxidizing currents of hydrogen peroxide and hydrogen are observed, while in the negative region, reducing currents of oxygen and hydrogen peroxide are observed, respectively. Potential regions wherein oxidizing currents and reducing currents are observed are defined as $E^A$ and $E^C$, respectively, and divided into the number $2^l (l=1, 2, 3, \ldots)$. Adoption of the number $2^l$ is for ease of processing by a computer. In this embodiment, they are divided into 8 levels ($l=3$) respectively, and each level is expressed by $E^A(n)$ and $E^C(n)$ ($n=1, 2, 3 \ldots 8$). Further, a potential thereat no electrode reaction of oxygen, hydrogen peroxide or hydrogen occurs is defined as $E_C$, and a potential at which a diffusion limiting current of oxidation reaction of hydrogen peroxide and hydrogen is obtained is defined as $E_1$.

Figure 18B:
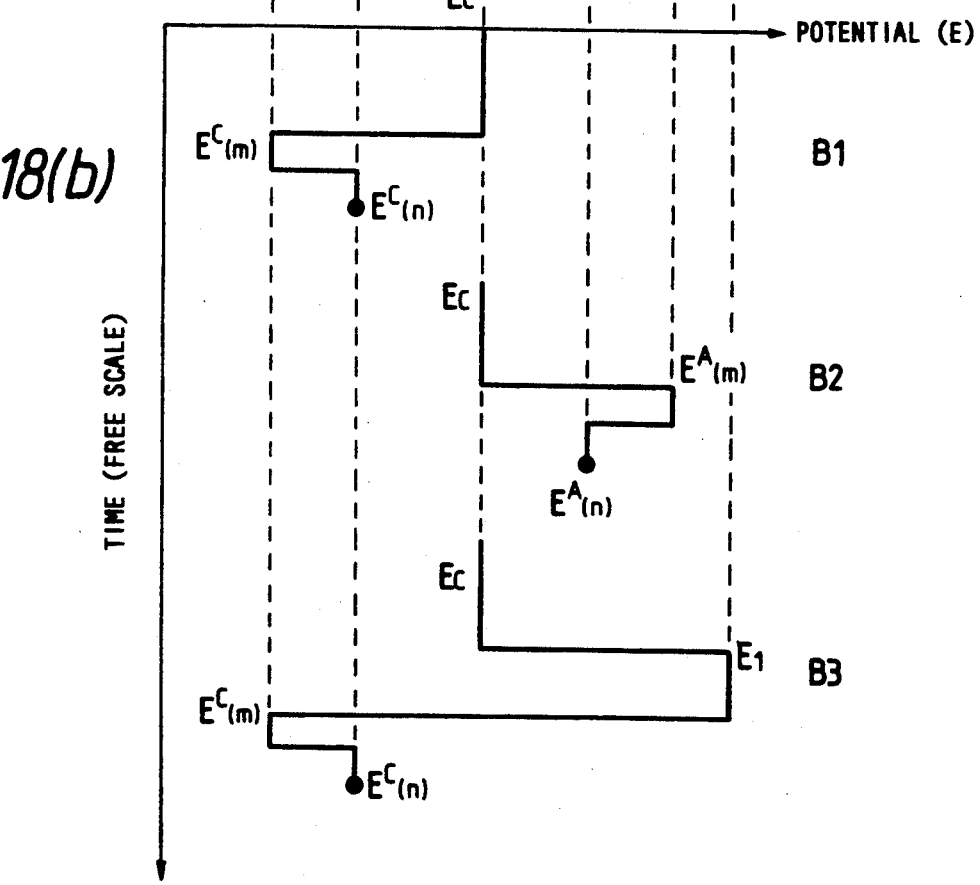

B1~B3 in FIG. 18(b) are three kinds of random pulse potential signals to be applied to the working electrode in the electrochemical sensor. These random pulse signals of three kinds are generated based on a normal pulse for obtaining $I^c_{l,Np}$ in embodiment 4, a normal pulse for obtaining $I^A_{l,Np}$, and a reverse pulse for obtaining $I^c_{l,Rp}$.

The first kind random pulse is applied in the order of $E_c \rightarrow E^c(m) \rightarrow E^c(n)$. In this embodiment $E^c$ is applied for one second, and $E^c(m)$ and $E^c(n)$ are applied for 0.05 second, respectively, and sampling of current values is conducted on completing $E^c(n)$. m and n represent a level (1~8) of division of $E^c$, respectively. There are 64 (8×8) combination patterns for potential of $E^c(m)$ and $E^c(n)$. Each current value corresponding to a combined m and n is stored in a data matrix $X^c_{Np}$ of 8×8. Because thus obtained $X^c_{Np}$ comprises operational data on reducing reactions of oxygen and hydrogen peroxide in water to measure, it provides almost the same quality of information on $C^*(O_2)$, $C^*(H_2O_2)$ as provided by $I^c_{l,Np}$ in the embodiment 4. $X^c_{Np}$, however, provides a larger quantity of information than $I^c_{l,Np}$, because the former includes existing data of as many as 64 points.

The second kind of random pulse is applied in the order of $E_c \rightarrow E^A(m) \rightarrow E^A(n)$. In this embodiment $E_c$ is applied for one second, and $E^A(m)$ and $E^A(n)$ are applied for 0.05 second, respectively, and sampling of current values is conducted on completing $E^A(n)$. In this case like the first one, a data matrix $X^A_{Np}$ of $8 \times 8$ corresponding to each combined m and n is obtained. Because thus obtained $X^A_{Np}$ comprises existing data on oxidization reactions of hydrogen peroxide and hydrogen in water to measure, it provides almost the same quality of information on $C^*$ ($H_2O_2$), $C^*$ ($H_2$), as provided by $I^A_{l,Np}$ in the embodiment 4.

The third kind of random pulse is applied in the order of $E_c \rightarrow E_1 \rightarrow E^c(m) \rightarrow E^c(n)$. In this embodiment, for the same respective periods of time as in the first kind random pulse, Ec, $E^c(m)$, $E^c(n)$ are applied, and $E_1$ for 0.1 second. After completing $E^c(n)$, sampling of current values was conducted. In this case alike the first and the second kinds, a data matrix $X^c_{Rp}$ of $8 \times 8$ corresponding to a combined m and n is obtained. The third kind random pulse differs from the first kind one in that $E_1$ is applied in each preceding stage of $E^c(m)$ and $E^c(n)$, one after another. This means that $X^c_{Rp}$ includes information on reducing reaction of oxygen generated through the oxidization of hydrogen peroxide in $E_1$, in addition to information on reduction of oxygen and hydrogen peroxide in water to test, of alike $I^c_{l,Rp}$ in the embodiment 4.

In the following, "Compression of pattern information" in (1) is explained in detail.

Here matrix $X^c(Rp-Np)$ is defined by equation (1), before a data matrix is transformed and compressed into $$X^c(Rp-Np) = X^c_{Rp} - X^c_{Np} \tag{1}$$

Through this operation, information on reducing reactions by oxygen and hydrogen peroxide in water to test is almost cancelled, thereby information on reducing reaction of the oxygen generated by oxidization of hydrogen peroxide is condensed in $X^c(Rp-Np)$. That is, $X^c(Rp-Np)$ provides almost the same quality of information as $I^c_{l,Rp} - I^c_{l,Rp}$ in the embodiment 4.

Data matrices $X^c(Rp-Np)$, $X^cNp$, and $X^ANp$ are transformed formed into matrices $Y^c(Rp-Np)$, $Y^cNp$, $Y^ANp$ respectively by equation (2).

$$Y = H \cdot X \cdot H \tag{2}$$

where.

$$H = \frac{1}{\sqrt{8}} \begin{pmatrix} 1 & 1 & 1 & 1 & 1 & 1 & 1 & 1 \\ 1 & -1 & 1 & -1 & 1 & -1 & 1 & -1 \\ 1 & 1 & -1 & -1 & 1 & 1 & -1 & -1 \\ 1 & -1 & -1 & 1 & 1 & -1 & -1 & 1 \\ 1 & 1 & 1 & 1 & -1 & -1 & -1 & -1 \\ 1 & -1 & 1 & -1 & -1 & 1 & -1 & 1 \\ 1 & 1 & -1 & -1 & -1 & -1 & 1 & 1 \\ 1 & -1 & -1 & 1 & -1 & 1 & 1 & -1 \end{pmatrix} \tag{3}$$

assuming that each component of the matrix Y is expressed by $$Y = \begin{pmatrix} y_{11} & y_{12} & \cdots & y_{18} \\ y_{21} & y_{22} & \cdots & y_{28} \\ \vdots & \vdots & & \vdots \\ y_{81} & y_{82} & \cdots & y_{88} \end{pmatrix} \tag{4}$$

Information belonging to X appears on a specific portion of Y consisting of 64 components, i.e., information on X dispersed on the 64 components of the same, is compressed into a specific set of several numbers of components in Y. More specifically in this embodiment, information on X is compressed on Y components, $y_{11}$, $y_{15}$, $y_{51}$, $y_{17}$, $y_{71}$. Further, from the components, $y_{11}$, $y_{15}$, $y_{51}$, $y_{17}$, $y_{71}$ for each $Y^c(Rp-Np)$, $Y^cNp$, $Y^ANp$ vectors $Z^c(Rp-Np)$, $Z^cNp$, $Z^ANp$ are obtained as follows.

$$Z = (y_{11}, y_{15}, y_{51}, y_{17}, y_{71}) \tag{5}$$

It has been thus explained that vectors $Z^c(Rp-Np)$, $Z^cNp$, and $Z^ANp$ contain highly compressed information on $C^*$ ($H_2O_2$), $C^*$ ($O_2$)$+C^*$ ($H_2O_2$), $C^*$ ($H_2O_2$)$+C^*$ ($H_2$), respectively.

Next, "Extraction of object information out of compressed pattern information" in (3) is explained in detail in the following.

A scalar field f is provided, to satisfy the following equation 6 in relation to a vector $Z^c(Rp-Np)$ obtained for a test water having a discretionary $C^*$ ($O_2$), $C^*$ ($H_2O_2$), $C^*$ ($H_2$).

$$C^*(H_2O_2) = f(Z^c(Rp-Np)) \tag{6}$$

Scalar fields f are obtained before hand for several kinds of test water having a discretionary $C^*$ ($O_2$) and $C^*$ ($H_2$) for known $C^*$ ($H_2O_2$). In this embodiment, this scalar field f is determined by means of a neural network system wherein each component of vector $Z^c(Rp-Np)$ is entered as input, and $C^*$ ($H_2O_2$) is outputted. Even for a test water with unknown value of $C^*$ ($H_2O_2$), it value can be calculated by equation 6.

In the same manner, scalar fields g and h are provided to satisfy the following equations (7) and (8) in relation to the vectors, $Z^cNp$ and $Z^ANp$, obtained for test water having a discretionary $C^*$ ($O_2$), $C^*$ ($H_2O_2$), $C^*$ ($H_2$)

$$C^*(O_2) = g(Z^cNp) - C^*(H_2O_2) \tag{7}$$

$$C^*(H_2) = h(Z^ANp) - C^*(H_2O_2) \tag{8}$$

The scalar fields g and h are obtained before hand for test water wherein $C^*$ ($H_2O_2$) and $C^*$ ($O_2$) are known, or $C^*$ ($H_2$ nsop $O_2$) and $C^*$ ($H_2$) are known, respectively. In this embodiment, by using a neural network wherein each component of vector $Z^cNp$ is entered as input and $C^*$ ($O_2$)$+C^*$ ($H_2O_2$) is outputted, and also another neural network wherein each component of vector $Z^ANp$ is entered and $C^*$ ($H_2$)$+C^*$ ($H_2O_2$) is outputted, the scalar fields g and h have been determined. Also for test water with unknown $C^*$ ($O_2$), $C^*$ ($H_2O_2$) and $C^*$ ($H_2$) these unknown values are possible to be obtained by equation (6), (7) and (8), respectively.

Figure 19:
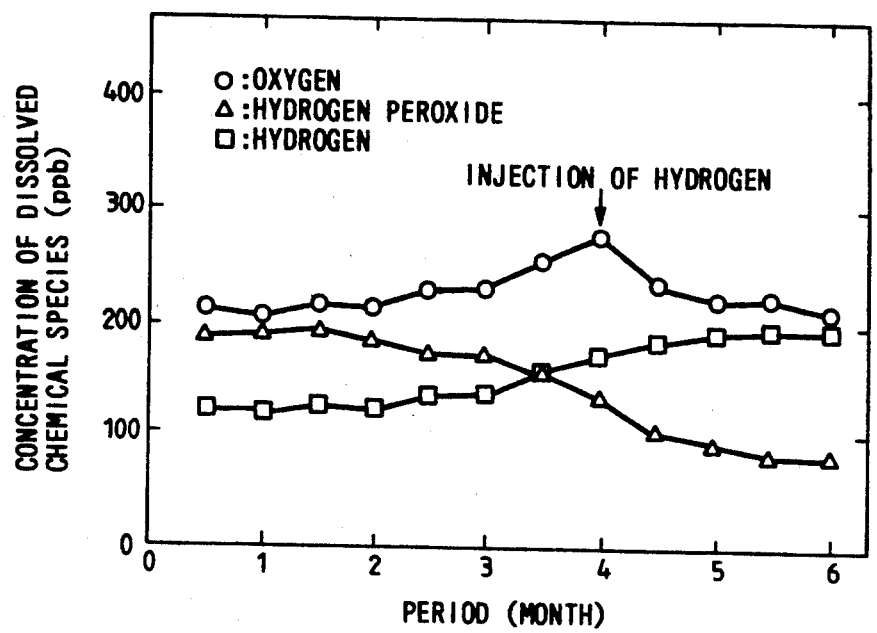
FIG. 19 illustrates separation and determination of dissolved oxygen, hydrogen peroxide and hydrogen by means of a random pulse method, in relation to time dependence and an effect of hydrogen injection.

FIG. 19 is a schematic diagram illustrating time-based variations of dissolved oxygen, hydrogen peroxide and hydrogen in the incore water, wherein the amount of the same was concurrently measured my means of the methods described above. When dissolved oxygen and hydrogen peroxide increase in concentration, the computer 6 instructs the gas injection system 8 to inject hydrogen according to the sequence shown in FIG. 1. It is shown in this figure that hydrogen injection was effective in the reduction of concentrations of oxygen and hydrogen peroxide.

In the following, a fundamental calculation method for the neural network is described.

First, each of the determined signal values $Z_1 \sim Z_n$ is multiplied by a weighting factor $W_{ji}$, and summed up in the following equation in form of a product-sum.

$$C_j(2) = \sum_{i=1}^{n} W_{ji}(2 \leftarrow 1) \cdot Z_i(1) \quad (1)$$

Where, $Z_i(1)$: a value of input layer (1st layer), $W_{ji}(2 \leftarrow 1)$: a weighting factor from a variable at i number of the input layer (1st layer) to a neuron element model at j number of the intermediate layer (2nd layer), $C_j(2)$: a total value of input at j number neuron element model in the intermediate layer (2nd layer).

For a neuron element model in the input layer, its output value is calculated by the following equation in accordance with a compensation for $C_j(2)$.

$$Z_j(2) = 1/(1 - e^{-c_j(2)}) \quad (2)$$

Figure 20:
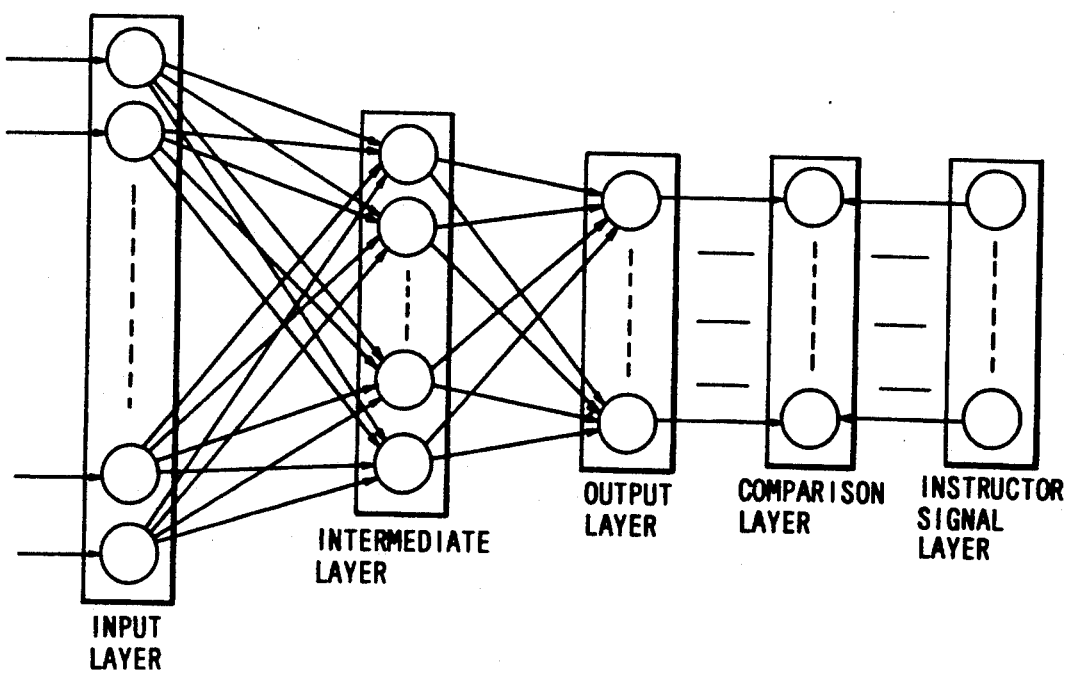
FIG. 20 is a diagram illustrating a structure of the neural network used in determining scalar fields f, g, and h.

Equation (2) is expressed by a relationship as shown in FIG. 20, i.e., a value ranging from "0" to "1" is obtained for $Z_j(2)$ corresponding to the value of $C_j(2)$. The calculated value $Z_j(2)$ is sent to the output layer, wherein the like calculation is executed.

An outline of calculation in the neural network is given below. The input value $Z_i(1)$ described above is entered in the input layer in FIG. 20, and its signal (value) is outputted to a neuron element model in the intermediate layer. In the neuron element model of the intermediate layer, $C_j(2)$ of product-sum of the same output put value $Z_i(1)$ and the weighting factor $W_{ij}(2 \leftarrow 1)$ is calculated by equation (1), and in accordance with its compensation, an output value $Z_j(2)$ to the output layer is determined by equation (2). Likewise, the output value $Z_j(2)$ further calculates $C_j(3)$ of a product-sum with a weighting factor $W_{ij}(3 \leftarrow 2)$ the intermediate layer (the 2nd layer) and the output layer (the 3rd layer by the following equation.

$$C_j(3) = \sum_{i=1}^{n} W_{ji}(3 \leftarrow 2) \cdot Z_i(2) \quad (3)$$

where, $Z_i(2)$: a value at the intermediate layer (the 2nd layer), $W_{ij}(3 \leftarrow 2)$: a weighting factor for variables from at i number in the intermediate layer (the 2nd layer) to a neuron model at j number in the output layer (the 3rd layer), $C_j(3)$: a total sum of input to a neuron element model at j number in the output layer (the 3rd layer).

Further according to a value of $C_j(3)$, an output value $Z_j(3)$ at the output layer is calculated by the following equation.

$$Z_j(3) = 1/(1 - e^{-c_j(2)}) \quad (4)$$

Thereby, a calculated value of $Z_j(3)$ for the output layer is obtained.

In order to execute a learning function in the neural network, a comparison layer and an instructor layer as shown in FIG. 20 are provided, and a signal from the output layer and a corresponding signal from the instructor layer are inputted in the comparison layer for comparison. Thereby values of weighting factors $W_{ji}(3 \leftarrow 2)$ and $W_{ji}(2 \leftarrow 1)$ are adjusted so as to reduce the difference or error in comparison.

In comparison once again of calculated signals obtained by equations (1) or (4) and instructor signals, there still arises like difference in comparison. Thereby once again, weighting factors $W_{ji}(3 \leftarrow 2)$ and $W_{ji}(2 \leftarrow 1)$ are adjusted still further to reduce the difference in values.

This process of adjustment of weighting factors $W_{ji}$ is repeated until the difference or error becomes sufficiently small. Because these weighting factors are given randomly at first by random number generation, errors are great in initial stages. Output signals, however, gradually approach instructor's signal values. The scalar fields f, g, and h are determined through these procedures. Here, symbols, c and z correspond to a concentration and a characteristic vector, respectively.

Such a method for adjusting errors as described above, is called the error reverse propagation method based on the technique devised by Rumelhart. A detailed description on the method is given in "Parallel Distributed Processing" by Rumelhart, MIT Press. vol. 1 (1986).

In accordance with the present invention, electrochemical analysis in the nuclear reactor is possible to be readily performed by means of a low impedance reference electrode. The reference electrode has a structure protected by a microscopic porous layer, therein dissolution of reference electrode ion from the reference electrode and incore water is possible to be controlled less than $10^{-12} mol/cm^2 \cdot s$ in volume of flux, providing an extremely long life (over 15 year life of silver in a 0.5 g silver/silver ion reference electrode) and a stable electrochemical analysis. Thereby, advanced technologies existing in the field of electrochemical analysis have been effectively applied to analysis of incore water quality, providing in-situ analysis of incore water for the first time as well as adequate incore information. By means of this technology, a plant operation status monitoring system using in-situ incore water quality data has been built.

Further, due to the development of a water quality sensing technique comprising an electrochemical cell structure of a long life exceeding a regular inspection period of a nuclear plant, and also due to the application of the neural network technique in processing water quality data, credibility of data is substantially increased, and reliability in the operation status supervisory system has been enhanced substantially.

The electrochemical electrode according to the present invention, unlike the electrochemical cell disclosed in Japanese Patent, Laid-Open No. 59-177474 (1984), does not necessiate the use of a resin membrane of high durability and selective permeability, thus enhancing its use under the environment at high temperatures and high pressure for a long period of time.

Further, in the prior art disclosed in Japanese Patent, Laid-Open, No. 56-77751 (1981), wherein by using zirconium oxide and the like as a hydrogen ion sensing element film, pH of high temperature water is measured. However, because zirconium oxide and the like have an extremely large impedance, they are not preferable in practice. On the other hand, in the present invention, because the ionic electrode member is surrounded by a porous ceramic or porous heat resistant plastic sheath, an electrochemical cell structure having an adequate impedance is possible to be made, without imposing excessive burden on output signal processing circuits and the like.

Because impedance of the reference electrode and the like according to the present invention is possible to be suppressed small enough reducing impedance in a feedbback circuit of a control amplifier, oscillation of output signals due to phase shift is easily prevented.

What is claimed is:

1. A monitoring system for plant operating conditions comprising: means for sampling consecutively information directly relating to high temperature water quality in an objective monitoring section of the plant for a certain period with an electrochemical water quality sensor disposed in said objective monitoring section; means for evaluating the water quality based on the sampled information; means for comparing the obtained results of the water quality evaluation with a predetermined reference value for the plant operation and manipulation; and means for displaying or recording necessary portions of said comparison result; wherein, said electrochemical water quality sensor is an electrochemical cell comprising a reference electrode member provided with an electrolyte layer containing ions of the reference electrode material, a porous layer which is made of ceramic or resin in contact with and surrounding the electrolyte layer and which is non-liquid-permeable but ion-permeable, a counter electrode member disposed in electrochemical relation with said electrolyte layer, said porous layer being in contact with and surrounding said reference electrode and said electrolyte so that said high temperature water does not directly contact said electrode and electrolyte, whereby dissolution of said reference electrode material into said high temperature water is substantially suppressed but said reference electrode is in electrochemical communication with said water, and terminals electrically contacting with said electrode members.

2. A monitoring system for plant operating conditions comprising: means for sampling consecutively information directly relating to high temperature water quality in an objective monitoring section of the plant in a period from one inspection to the next inspection of the plant with an electrochemical water quality sensor disposed in said objective monitoring section of the plant; means for evaluating the water quality based on the sampled information; means for comparing the obtained results of water quality evaluation with a predetermined reference value for the plant operation and manipulation; and means for displaying or recording necessary portions of said comparison result; wherein said electrochemical water quality sensor comprises an electrochemical reference electrode provided with a solid electrolyte layer containing ions of the reference electrode member, a porous ceramic layer in contact with and surrounding the electrolyte layer, a counter electrode member disposed in electrochemical relation with said electrolyte layer, a heat resistant porous ceramic overcoat layer surrounding said ceramic layer which is non-liquid-permeable but ion-permeable, said porous layer being in contact with surrounding said reference electrode and said electrolyte so that said high temperature water does not directly contact said electrode and electrolyte, whereby dissolution of said reference electrode material into said high temperature water is substantially suppressed but said reference electrode is in electrochemical communication with said water, and terminals electrically contacting said electrode members.

3. A monitoring system for plant operating conditions comprising: means for sampling consecutively information directly relating to high temperature water quality in an objective monitoring section of the plant in a predetermined period with a electrochemical water quality sensor disposed in said objective monitoring section of the plant and in which the high temperature water in said objective monitoring sections contacts electrochemically with electrolyte through a porous material, said electrochemical water quality sensor comprising a reference electrode, an electrolyte body in contact with said reference electrode, a counter electrode disposed in electrochemical relation with said reference electrode, a porous layer of water-impermeable, ion-permeable and heat resistant material, and terminal electrically contacting with said electrodes, said porous layer being in contact with and surrounding said reference electrode and said electrolyte so that said high temperature water does not directly contact said electrode and electrolyte, whereby dissolution of said reference electrode material into said high temperature water is substantially suppressed but said reference electrode is in electrochemical communication with said water; means for analyzing the water quality based on the sampled information; means for comparing the obtained results of water quality analyzation with a predetermined reference value for the plant operation and manipulation; and means for displaying or recording necessary portions of the resulting comparison.

4. A monitoring system for plant operating conditions comprising: means for sampling consecutively information directly relating to water quality of high temperature water in an objective monitoring section of the plant in a predetermined period with an electrochemical water quality sensor disposed in said objective monitoring section of the plant and in which the high temperature water in said objective monitoring section contacts electrochemically with an electrolyte through a porous material substantially suppressing dissolution of the electrolyte to the high temperature water, said electrochemical water quality sensor comprising a reference electrode in contact with an electrolyte material, a heat resistant, insoluble, a porous material layer in contact with and a surrounding said reference electrode and said electrolyte material so as to substantially isolate the electrode and electrolyte from the water, a terminal electrically contacting said reference electrode, a pH electrode disposed in electrochemical relation with said reference electrode and surrounded by the heat resistant, insoluble, porous material, and a terminal electrically contacting said pH electrode, whereby dissolution of said reference electrode and pH electrode into high temperature water is substantially suppressed but said electrodes are electrochemically communicated with said high temperature water; means for analyzing the water quality based on the sampled information; means for comparing the obtained results of water quality analyzation result with a predetermined reference value for the plant operation and manipulation; and means for displaying and/or recording necessary portions of the resulting comparison information.

5. A monitoring system for plant operating conditions comprising: means for analyzing consecutively water quality in a circulation water line or a storage water line in a period from a periodic inspection to the next inspection of the plant with an electrochemical sensor disposed in said objective monitoring section of the plant including high temperature water, said electrochemical sensor comprising a reference electrode in contact with an electrolyte material, a heat resistant, insoluble, porous material layer in contact with an completely surrounding said reference electrode and said electrolyte material, a terminal electrically contacting said reference electrode, a pH electrode disposed in electrochemical relation with said reference electrode and surrounded by the heat resistant, insoluble, porous material, and a terminal electrically contacting said pH electrode, whereby dissolution of said reference electrode and pH electrode into high temperature water is substantially suppressed but said electrodes re electrochemically communicated with said high temperature water; means for displaying the analyzed result; means for selecting a predetermined reference value for the plant operation and manipulation in response to the analyzed water quality result; means for predicting variation of said reference value based on the mutual relationship between the analyzed result and the reference value for the plant operation and manipulation; and means for controlling water quality.

6. A monitoring system for plant operating conditions comprising: means for analyzing consecutively water quality in a circulation water line or a storage water line in a period from a periodic inspection to the next inspection of the plant with an electrochemical sensor disposed in said objective monitoring section of the plant including high temperature water and for outputting data relating to at least pH, an amount dissolved oxygen and concentration of dissolved hydrogen, said electrochemical sensor comprising a reference electrode, an electrolyte body in contact with said reference electrode, a counter electrode disposed in electrochemical relation with said electrolyte a porous layer of water impermeable, ion-permeable and heat resistant material, and terminals electrically contacting said electrodes, said porous layer being in contact with and substantially isolating said electrode and electrolyte from the water, whereby dissolution of said reference electrode material into said high temperature water is substantially suppressed but said reference electrode is electrochemically communicated with said water; means for displaying the analyzed result; means for selecting a predetermined reference value for the plant operation and manipulation in response to the analyzed water quality result; means for predicting variation of said reference value based on the mutual relationship between the analyzed result and the reference value for the plant operation and manipulation; and means for controlling water quality.

7. A monitoring system for plant operating conditions according to claim 1, wherein said porous layer is a ceramic layer with microscopic apertures covering a solid electrolyte or an electrochemical material formed over electrodes of supporting member.

8. A monitoring system for plant operating conditions according to claim 1, wherein said sensor comprises at least two kids of sensors for sensing dissolving hydrogen (DH), dissolving oxygen (DO), hydrogen ion concentration (pH), reference electrode (ECP), solution electric conductivity (S), dissolving hydrogen peroxide ($DH_2O_2$) and crack (M).

9. An electrochemical reference electrode comprising: a solid electrolyte layer containing ion of the electrode member, a porous ceramic layer or porous resin layer surrounding the same, which is non-liquid-permeable, an electrode member electro-chemically contacting with said electrolyte layer, a heat resistant porous overcoat layer surrounding said ceramic layer or resin layer, and a terminal electrically contacting with said electrode material.

10. An electrochemical electrode comprising an electrolyte layer composed of halogenated substance of the electrode, a porous ceramic layer or porous resin layer surrounding the same, which is non-liquid-permeable, an electrode member electrochemically contacting with said electrolyte layer, a sheath protecting said ceramic layer or resin layer and providing an aperture for communicating part of said ceramic layer or resin layer with a liquid to be tested, and a terminal electrically contacting with said electrode member.

11. An electrochemical electrode characterized by comprising a solid electrolyte layer containing positive ion and halogen ion of the electrode member, a porous ceramic layer or resin layer surrounding the same, a porous insulation layer surrounding said porous ceramic layer or resin layer preventing liquid permeance but allowing ion permeance, a metal electrode member electrochemically contacting with said electrolyte layer, a sheath protecting said ceramic layer or resin layer and providing an aperture for communicating part of said ceramic layer or resin layer with a liquid to test, and a terminal electrically contacting with said electrode member.

12. An electrochemical electrode comprising a solid electrolyte layer containing an oxide of the electrode member, a porous ceramic layer or resin layer surrounding the above, a porous insulation layer surrounding said porous ceramic layer or resin layer preventing liquid permeance but allowing ion permeance, a metal electrode member electrochemically contacting with said electrolyte layer, a sheath protecting said ceramic layer or resin layer and providing an aperture for communicating part of said ceramic layer or resin layer with a liquid to be tested, and a terminal electrically contacting with said electrode member.

13. A monitoring system for plant operating conditions according to claim 2, wherein said porous ceramic layer is a ceramic layer with microscopic apertures covering a solid electrolyte formed over said electrodes.

14. A monitoring system for plant operating conditions according to claim 2, wherein said sensor comprises at least two kinds of sensors for sensing dissolved hydrogen (DH), dissolved oxygen (DO), hydrogen ion concentration (pH), reference electrodes (ECP), solution electric conductivity (S), dissolved peroxide ($DH_2O_2$) and crack length (M).

15. A monitoring system for plant operating conditions according to claim 3, wherein said porous layer is a ceramic layer with microscopic apertures covering a solid electrolyte formed over said electrodes.

16. A monitoring system for plant operating conditions according to claim 3, wherein said sensor comprises at least two kinds of sensors for sensing dissolved hydrogen (DH), dissolved oxygen (DO), hydrogen ion concentration (pH), reference electrode (ECP), solution electric conductivity (S), dissolved peroxide ($DH_2O_2$) and crack length (M).

* * * * *